United States Patent [19]

McCapra

[11] Patent Number: 5,705,622

[45] Date of Patent: Jan. 6, 1998

[54] SENSITIZER CONJUGATES CONTAINING PORPHYRINS

[75] Inventor: Frank McCapra, Seaford, Great Britain

[73] Assignee: London Diagnostics, Inc., Eden Priarie, Minn.

[21] Appl. No.: 623,410

[22] Filed: Mar. 28, 1996

Related U.S. Application Data

[60] Division of Ser. No. 984,296, Dec. 1, 1992, Pat. No. 5,516,636, which is a continuation-in-part of Ser. No. 360,188, Jun. 1, 1989, abandoned, which is a continuation-in-part of Ser. No. 204,055, Jun. 8, 1988, abandoned.

[51] Int. Cl.[6] .......................... C07H 21/02; C07H 21/04; C12Q 1/68

[52] U.S. Cl. ........................ 536/23.1; 435/4; 435/5; 435/6; 435/7.2; 436/501; 530/300; 530/350; 536/24.1; 536/24.3; 536/24.31; 536/24.32; 536/24.33; 935/77; 935/78

[58] Field of Search ............... 435/4–6, 7.2; 436/501; 530/300, 350; 536/23.1, 24.1, 24.3–24.33; 935/77, 78

[56] References Cited

U.S. PATENT DOCUMENTS

| | | | |
|---|---|---|---|
| 4,935,498 | 6/1990 | Sessler et al. | 534/15 |
| 5,340,716 | 8/1994 | Ullman et al. | 435/6 |
| 5,516,636 | 5/1996 | McCapra | 435/6 |

OTHER PUBLICATIONS

Shimidzu et al. (1992) Nineteenth Symposium on Nucleic Acid Chemistry, Fukuoka, Japan, pp. 97–98.

*Primary Examiner*—Ardin H. Marschel
*Attorney, Agent, or Firm*—Dorsey & Whitney

[57] ABSTRACT

Specific binding assays are disclosed which utilize a sensitizer as a label. Such sensitizers include any moiety which, when stimulated by "exaitation" with radiation of one or more wavelengths or other chemical or physical stimulus (e.g., electron transfer, electrolysis, electroluminescence or energy transfer), will achieve an excited state which (a) upon interaction with molecular oxygen will produce singlet molecular oxygen, or (b) upon interaction with a leucodye will assume a reduced form which can then be returned to its original unexcited state by interaction with molecular oxygen resulting in the production of hydrogen peroxide. Either interaction with the excited sensitizer will, with the addition of other reagents, produce a detectable signal.

4 Claims, 2 Drawing Sheets

SENSITIZER CONJUGATES CONTAINING PORPHYRINS

RELATED PATENT APPLICATIONS

This application is a divisional application of application Ser. No. 07/984,296, filed Dec. 1, 1992, now U.S. Pat. No. 5,516,636; which is a continuation-in-part of application Ser. No. 360,188, filed Jun. 1, 1989, now abandoned; which is a continuation-in-part of application Ser. No. 204,055, filed Jun. 8, 1988, now abandoned.

BRIEF DESCRIPTION OF THE INVENTION

Compositions and specific binding assays which utilize a sensitizer as a label conjugated with a specific binding material, in which the sensitizer is raised to the excited state and transfers energy to or electrons from other compounds in association with it and such other compounds produce a detectable signal that can be monitored and/or quantitated.

BACKGROUND OF THE INVENTION

Most organic reactions are carried out between molecules in the ground state. However, photochemical reactions, utilizing light of a specific wavelength range, promote molecules to an electronically excited state. Electrons can move from the ground-state energy level of the molecule to a higher level with this application of outside energy.[1] The following table (March, supra, page 210) illustrates physical processes undergone by excited molecules:[2]

| | |
|---|---|
| $S_0 + h\nu \to S_1^v$ | Excitation |
| $S_1^v \leadsto S_1 + \text{heat}$ | Vibrational relaxation |
| $S_1 \to S_0 + h\nu$ | Fluorescence |
| $S_1 \leadsto S_0 + \text{heat}$ | Internal conversion |
| $S_1 \leadsto T_1^v$ | Intersystem crossing |
| $T_1^v \leadsto T_1 + \text{heat}$ | Vibrational relaxation |
| $T_1 \to S_0 + h\nu$ | Phosphorescence |
| $T_1 \leadsto S_0 + \text{heat}$ | Intersystem crossing |
| $S_1 + A_{(S_0)} \to S_0 + A_{(S_1)}$ | Singlet—singlet transfer (photosensitization) |
| $T_1 + A_{(S_0)} \to S_0 + A_{(T_1)}$ | Triplet-singlet transfer (photosensitization) |

Some compounds will assume excited triplet[3] states upon "excitation" by exposure to a certain wavelength of light. These compounds ("sensitizers" or "photosensitizers") can interact with various other compounds ("acceptors") and transfer energy to or electrons from the acceptors, thus returning the sensitizer to its unexcited or ground state. Most compounds will assume the excited singlet[4] state upon "excitation." A photosensitizer in its triplet state is capable of converting ground-state oxygen (a triplet) to an excited singlet state. The singlet oxygen can result in the production of a detectable "signal" which can be monitored and/or quantitated. In the context of this invention, a sensitizer is a molecule with a Chromophore capable of absorbing light so that it becomes electronically excited. The best sensitizers are those which undergo Intersystem Crossing to the triplet state, i.e., involves the sequence: $S_0+h\nu \to S_1^{84}$, $S_1 \leadsto T_1^{84}$, and $T_1+A_{(S_0)} \to S_0+A_{(T_1)}$.

[1] According to March, Advanced Organic Chemistry, 3rd Ed., 1985, John Wiley & Sons, New York, N.Y., at p. 202: "Since the energy levels of a molecule are quantized, the amount of energy required to raise an electron in a given molecule from one level to a higher one is a fixed quantity. Only light with exactly the frequency corresponding to this amount of energy will cause the electron to move to the higher level. If light of another frequency (too high or too low) is sent through a sample, it will pass out without a loss in intensity, since the molecules will not absorb it. However, if light of the correct frequency is passed in, the energy will be used by the molecules for electron promotion and hence the light that leaves the sample will be diminished in intensity or altogether gone." At page 204, March points that though promotion of an electron to either a singlet or triplet excited state would seemingly be possible "depending upon the amount of energy added" this is often not the case because certain transition are "forbidden." For example, singlet-triplet and triplet-singlet transitions are forbidden, "whereas singlet-single and triplet-triplet transitions are allowed."
[2] The superscript v indicates vibrationally excited state: excited states higher than $S_1$ or $T_1$ are omitted.
[3] The condition within a molecule in which two unpaired electrons have the same spin.
[4] The condition within a molecule in which all spins are paired.

The development of singlet oxygen is reviewed in "Singlet Molecular Oxygen," edited by A. Paul Schaap (Dowden, Hutchinson and Ross, Stroudsburg, Pa. 1976), in the Introduction as follows:

The oxidation of organic and biological substrates under the influence of light, oxygen, and a sensitizer has been under investigation since the report by Fritzsche in 1867 that photoxygenation of naphthacene yields a peroxide. Two general types of photosensitized oxygenation are observed: (1) the excited sensitizer serves to initiate a free-radical propagated antoxidation, and (2) the reactive intermediate is an electronically excited state of molecular oxygen (singlet oxygen) produced by the transfer of energy from the excited sensitizer to oxygen. An example of photochemically initiated autoxidation is the benzophenone-sensitized oxidation of isopropyl alcohol in the presence of oxygen, initially investigated by Bäckström. Early photooxygenation reactions, which were subsequently shown to involve singlet oxygen, include the photooxygenation of rubrene investigated by Moureu, Dufraisse, and Dean . . . and the dye-sensitized photooxygenation of ergosterol investigated by Windaus and Brunken . . . . However, it was the classic synthesis of ascaridole from α-terpinene by Schenck and Ziegler in 1944 that prompted extensive preparative and mechanistic investigations of photooxygenation.

In 1931, Kautsky and de Bruijn . . . proposed that dye-sensitized photooxygenation involved the transfer of electronic excitation energy from the exalted sensitizer to oxygen to produce a "reactive, metastable state of the oxygen molecule." At the time of Kautsky's proposal, only the $^1\Sigma_g^+$ excited state of oxygen had been observed spectroscopically, and this was assumed to be the reactive oxygen species. Following the report by Ellis and Kneser in 1933 of the $^1\Delta_g$ state of oxygen, both states of oxygen were considered as possible reactants in photooxygenation . . . . Kautsky supported his proposed mechanism with a series of elegant experiments that should have put to rest the sensitizer-oxygen complex mechanism. It was observed that photooxygenation was possible even when the sensitizer and the acceptor were physically separated on different grains of silica gel, which demonstrated that only a diffusible molecule such as $^1O_2$ could be the reactive species. In spite of these results, the Kautsky mechanism was almost totally disregarded and was not revived until the independent generation of singlet oxygen with NaOCl and $H_2O_2$ and with the electrodeless discharge . . . .

Molecular oxygen, a ground-state triplet with paramagnetic and diradical-like properties, has two low-lying singlet excited states, $^1\Delta_g$ and $^1\Sigma_g^+$. As the transition of $^1\Delta_g$ to $^3\Sigma_g^-$ is spin-forbidden, $^1\Delta_g$ is a relatively long-lived species. The $^1\Sigma_g^+$ state is relatively short-lived with a spin-allowed transition to $^1\Delta_g$. The life-time of the $^1\Sigma_g^+$ is sufficiently short that all singlet oxygen chemistry in solution involves the $^1\Delta_g$ state.

In addition to photosensitization, several alternative methods for the generation of singlet oxygen have been developed: the reaction of sodium hypochlorite with hydrogen peroxide, the thermal decomposition of phosphite ozonides, the decomposition of epidioxides, the reaction of potassium superoxide in water, the self-reaction of sec-peroxy radicals, and microwave discharge through gaseous oxygen.

| Electronic states of molecular oxygen | | | |
|---|---|---|---|
| State | Energy above ground State (k cal) | Lifetime in solution (s) | Radiative lifetime at zero pressure |
| $^1\Sigma^+_g$ | 37.5 | $10^{-9}$ to $10^{-12}$ | 7.1 s |
| $^1\Delta_g$ | 22.5 | $10^{-3}$ to $10^{-6}$ | 45 min. |
| $^3\Sigma^-_g$ | 0 | | |

The reactions of singlet oxygen with a wide variety of organic substrates are discussed . . . . Singlet oxygen exhibits three modes of reaction with alkenes: 1,4-cycloaddition with conjugated dienes to yield cyclic peroxides, an "ene"-type reaction to form allylic hydroperoxides, and 1,2-cycloaddition with olefins to give 1,2-dioxetanes, which cleave thermally to carbonyl-containing products. Other reactions of singlet oxygen include oxidation of sulfides to sulfoxides and sulfones and addition to heterocycles such as pyrroles, furans, oxazoles, imidazoles, and thiophenes. Singlet oxygen also reacts with such biologically important substrates as fatty acids, purines, pyrimidines, DNA, PNA, amino acids (tyrosine, tryptophan, methionine, cystine, histidine) and various proteins. The possible role of singlet oxygen in biological oxidations has been considered by several investigators.

Chapter 8 of the Schaap, supra, text, is a translation of an article by Kautsky et al., entitled: "Photosensitized Oxidation Mediated By A Reactive, Metastable State Of The Oxygen Molecule," in which singlet oxygen generated by the reaction of ground state oxygen and an excited photosensitizer, is transmitted to an acceptor. The acceptor was defined as follows (p. 35):

"The acceptor has to be a compound that is polarly adsorbed by silica gel and which, under the given conditions, is not oxidized by normal oxygen but by activated oxygen. These requirements are met by leuco compounds of triphenylmethane dyestuffs. They possess the special advantage that, when oxidized, they are converted into intensely colored dyestuffs; therefore, they can serve as visible indicators for very small amounts of activated oxygen. The first experiments were carried out with p-leucaniline, and the later experiments with leucomalachite green, which is more suitable because the blue color of malachite green formed during the oxidation of this compound is easier to distinquish from the above-mentioned rust-red coloration of the trypaflavine adsorbate arising upon extended irradiation."

This is illustrated in the following:

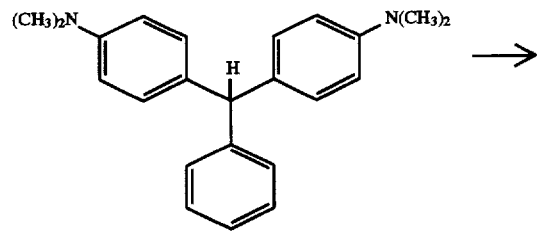

Colorless (leucomalachite green)

→

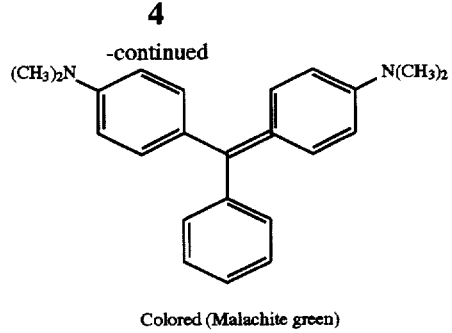

Colored (Malachite green)

Luminescence is a genetic term covering a wide range of processes which produce light following electronic excitation through the absorption of any form of energy. Chemiluminescene or "cold light", may be defined as the emission of light as a result of an exergonic chemical reaction at temperatures below that required for incandescence. Bioluminescene or "living light" is a special case of chemiluminescence in biological systems in which the ongoing chemical reaction is catalysed by an enzyme or produced by photoproteins.

The overall efficiency of light emission or quantum yield ($\phi$) of a chemiluminescent reaction is defined, in Einsteins, as the number of photons produced by a mole of substrate. It is the product of the chemical $\phi_c$, excitation $\phi_e$, and fluorescence $\phi_f$ efficiencies as expressed below.

$$\phi=\phi_c\phi_e\phi_f$$

The quantum yield varies considerably from 0.88 for firefly bioluminescence to as low as $10^{-15}$. Typical values suitable for analytical applications are in the range 0.01 to 0.34.

There is much literature on tagging of a specific binding material with a compound that evokes a detectable signal. The signal may come from the decay of the label such as by emission of a radiolabeled form or by the decomposition of the label as in the case of luminescent labels. Other systems utilize biological processes, such as an enzyme-catalyzed reaction. The capabilities of such labeling systems are illustrated in Table A. Among the most sensitive of such systems are chemiluminescent immunoassays employing select classes of acridinium esters.

TABLE A

| Detection Limits Of A Number Of Widely Used Labels In Immunoassay | | |
|---|---|---|
| Immunoassay | Label | Typical Detection Limit/Mole |
| Radioisotopes | $^3$H | $1 \times 10^{-16}$ |
| | $^{125}$I | $1 \times 10^{-18}$ |
| Chemiluminescence | Isoluminol | $5 \times 10^{-15}$ |
| | Acridinium Esters | $2 \times 10^{-18}$ |
| Bioluminescence | Firefly Luciferin-Luciferase | $10^{-14} - 10^{-15}$ |
| Enzyme with CL Detection | Peroxidase Luminol/Enhancer | $8 \times 10^{-17}$ |
| | Glucose-6-phosphate dehydrogenase Isoluminol | $1 \times 10^{-18}$ |
| Fluorescence (delayed fluorescence) | Europium | $2 \times 10^{-17}$ |
| | Fluorescein | $1 \times 10^{-13}$ |
| Enzyme | β-Galactosidase | $2 \times 10^{-18}$ |
| | Horseradish Peroxidase | $3 \times 10^{-18}$ |
| | Alkaline Phosphatase | $5 \times 10^{-19}$ |

There is substantial literature about such labels, see e.g., McCapra, "Chemiluminescence of Organic Compounds," in Progress in Organic Chemistry, vol. 8, Carruthers and Sutherland ed., Wiley & Sons (1973); Kohen, Bayer, Wilechek, Barnard, Kim, Colleins, Beheshti, Richardson and McCapra, "Development Of Luminescence-Based Immunoassays For Haptens And For Peptide Hormones," pp. 149–158, in *Analytical Applications Of Bioluminescence and Chemiluminescence*, Academic Press, Inc. (1984); Richardson, Kim, Barnard, Collins and McCapra, *Clinical Chemistry*, vol. 31, no. 10, pp. 1664–1668 (1985); McCapra, "The Application of Chemiluminescence in Diagnostics," 40th Conference of the American Association of Clinical Chemists, New Orleans, La., Jul. 28, 1988; McCapra, "The Chemiluminescence Of Organic Compounds," *Quarterly Reviews*, vol. 20, pp. 485–510 (1966); McCapra, "The Chemiluminescence Of Organic Compounds," *Pure and Applied Chemistry*, vol. 24, pp. 611–629 (1970); McCapra, "The chemistry of bioluminescence," *Proceedings Of Royal Society*, vol. B215, pp. 247–278 (1982); McCapra and Beheshti, "Selected Chemical Reactions That Produce Light," *Bioluminescence and Chemiluminescence: Instruments and Applications*, CRC Press, vol. 1, Chapter 2, pp. 9–37 (1985); McCapra, "Chemiluminescent Reactions of Acridines," Chapt. IX, *Acridines*, R. M. Acheson, Ed., pp. 615–630, John Wiley & Sons, Inc. (1973); McCapra, "Chemical Mechanisms in Bioluminescence," *Accounts Of Chemical Research*, vol. 9, no. 6, pp. 201–208 (June 1976); and in many other publications and presentations on the subject.

The use of certain dye as labels is well recognized in the literature, see, e.g., Rinderknecht, *Nature*, 193, 4811, p. 167 (1962) who describes the labeling of proteins with fluoresceinisothiocyanate and dimethylaminonaphthalene sulphonyl chloride; Mann et al., Method of Enzymology, 26, pp. 28–42, see pp. 36–39 (1972) who describe fluorescein, $^{14}$C-labeling of amino groups, incorporation of dinitrophenyl and trinitrophenyl; and Riggs et al., *American can Journal of Pathology*, 34, 6, pp. 1081–1097 (1958) labeled serum with

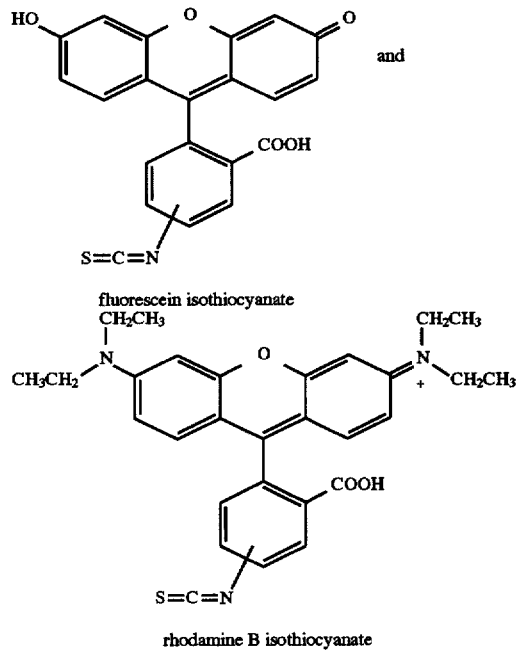

fluorescein isothiocyanate rhodamine B isothiocyanate and used the two to determine by staining the presence of the antigen; Cherry et al., *Stain Technology*, "Evaluation Of Commercial Fluorescein Isothiocyanates Used In Fluorescent Antibody Studies," 44, 4, pp. 179–186 (1969) describe comparable information.

Molecular Probes, Inc., P.O. Box 22010, (4849 Pitchford Avenue) Eugene, Oreg. 97402-0414, offers an extensive variety of fluorescent probes for use in labeling applications. A substantial number of the labeling compound listed below are taken from their Handbook Of Fluorescent Probes and Research Chemicals.

THE INVENTION

The invention relates to a specific binding assay comprising a sensitizer as a label to a specific binding material that is employed in a specific binding reaction for the presence of an analyte in a sample undergoing the assay. A binding occurs between the labeled specific binding material and the analyte in the sample. The sample is exposed to an energy source to bring the sensitizer to its excited state where it will donate its excess energy. The assay contains another molecule that functions as an acceptor for the energy transmitted by donor. The energy from the donor is transmitted to the acceptor, and a signal is evoked that is correlated to the presence and/or amount of analyte in the sample.

The invention involves specific binding assays that use a photosensitizer ("sensitizer") as a label. In the assay, a sensitizer is attached as a label to a specific binding material that is employed in a specific binding reaction for the presence of an analyte in a sample undergoing the assay. The sample is exposed to an appropriate energy source, preferably a prescribed level of radiation, such as light of a specific wavelength range, in order to bring the sensitizer to the excited triplet state where it can donate it excess energy. The sensitizer in the triplet state (the "donor") interacts with another molecule (an "acceptor" for the energy transmitted by donor) that is present in the assay and a signal is evoked that is correlated to the presence and/or amount of analyte in the sample. The signal is used to determine the presence and/or amount of analyte in the sample. The invention provides a most sensitive detection system for determining the presence of an analyte in a sample.

Energy emitted from the excited sensitizer directly or indirectly causes the signal to be produced. The signal is typically created as a result of the donor-acceptor interaction between the excited triplet state sensitizer and the "other molecule" that is called the acceptor. The sensitizer returns to its original state when its energy is passed to the acceptor, preferably by a triplet-singlet transfer. The sensitizer is still present in association with unaffected acceptor and thus available for another excitation, followed by triplet-singlet transfer to the residual acceptor and the creation of an even greater signal. This excitation and energy transfer may be repeated many times all within an exceptionally short period of time so that the use of a sensitizer as a label provides the added advantage of amplifying the signal, thus greatly increasing the sensitivity of the assay. In this sense, the sensitizer label functions as a recycling energy pump that causes a uniquely high level signal creating the capability of detection limits that are as much as a thousand fold greater than those provided by the most current state of the art immunoassay and DNA assay systems.

The attractiveness of the invention can be seen when compared with more conventional assay systems. In the conventional assays systems, the label forms the signal directly such as by a color change, emission of light or radiation. For example, in chemiluminescent labeled systems, the chemiluminescent label is oxidized to directly emit photons, the signal. The intensity of the signal of a chemiluminescent compound is correlated with the mount of chemiluminescent compound present and the chemiluminescence efficiency of the chemiluminescent compound. If all of the chemiluminescent compound is labeled material, then there is a finite signal intensity that one can generate and that is correlated with the amount of label attached to the specific binding material and the efficiency of the association of the specific binding material to bind directly or indirectly to the analyte. However, in the case of this invention, a much larger amount of unlabeled chemiluminescent compound can be produced in the assay. Since the acceptor of the energy is present in great excess over the label, the repeated recycling of the photosensitizer under the influence of the continuous irradiation by the exciting light, will lead to amplifications many fold over the concentration of the label. The sensitizer can, in principle, transform several million times its own concentration of the acceptor. The acceptor thus transformed is either colored or capable of emitting chemiluminescence as described or inducing other molecules in excess to do this. The only limit to the amount of acceptor transformed into a detectable material is set by the photostability of the photosensitizing label.

In the context of this invention, "sensitizer" (or "photosensitizer") means the label conjugated with the specific binding material that, when excited by radiation of one or more wavelengths or other chemical or physical stimulus (e.g., electron transfer, electrolysis, electroluminesence or energy transfer), achieves an excited triplet state and (a) upon subsequent reaction with molecular oxygen produces singlet molecular oxygen, or (b) upon subsequent reaction with a leucodye evokes a color change, or (c) upon subsequent reaction with a leucodye, whereby the sensitizer will assume a reduced form from which it can be returned to its original state by reaction with singlet oxygen resulting in the production of hydrogen peroxide. The hydrogen peroxide can be used as a signal to determine the amount of analyte or be used in chemical reactions that will signal the amount of analyte.

Either of the reactions of the excited sensitizer will, with the addition of other reagents in some cases but not in others, produce a detectable signal. In the first case, the singlet molecular oxygen reacts with an olefin (i) to form a dioxetan that decays upon heating to emit a detectable photon, or (ii) to form a peroxide that can either (1) decay upon heating to emit a detectable photon or (2) oxidize a chromogen to produce a detectable color change or fluorescence.

In the second case, the oxidized leucodye will produce a detectable color change or fluoresce. As an offshoot of the second case, hydrogen peroxide produced by recycling the reduced sensitizer to the presence of singlet oxygen, can be detected as a result of the oxidation of a chromogen resulting in a detectable color change or fluorescence or the oxidation of a chemiluminescent compound producing a detectable photon. Because of the "pumping" capabilities derived from the oxidation and reduction of the sensitizer, greater amounts of the detectable signal are obtained making detection considerably more sensitive to low concentrations of analyte being subjected to detection. In a variation on the above, the singlet oxygen may react with a leucodye to induce a color change.

The invention contemplates the use of the inventive assay system in an assay kit that includes the sensitizer conjugate, olefins and/or leucodyes. The specific binding assay kit typically comprises a first vial containing a sensitizer conjugate, the sensitizer conjugate comprising a sensitizer attached to a specific binding material in which the sensitizer is a moiety that is induced to an excited state by radiation such that it is reactable with (a) molecular oxygen to produce singlet molecular oxygen or (b) a leucodye to form a reduced form of the sensitizer that is oxidizable to its original state by reaction with oxygen thereby producing hydrogen peroxide; and a second vial containing at least one of an olefin and a leucodye. Preferably, the sensitizer is a dye, such as a porphyrin, a metalloporphyrin, an aromatic hydrocarbon and a flavin derivative. In a preferred embodiment, the second vial contains an olefin, preferably a substituted olefin such as one that has at least one substitution which is an electron donating group and/or one that possesses at least two substitution which are joined to form a ringed moiety which is fluorescent.

DETAILED DESCRIPTION OF THE INVENTION

Figure 1:
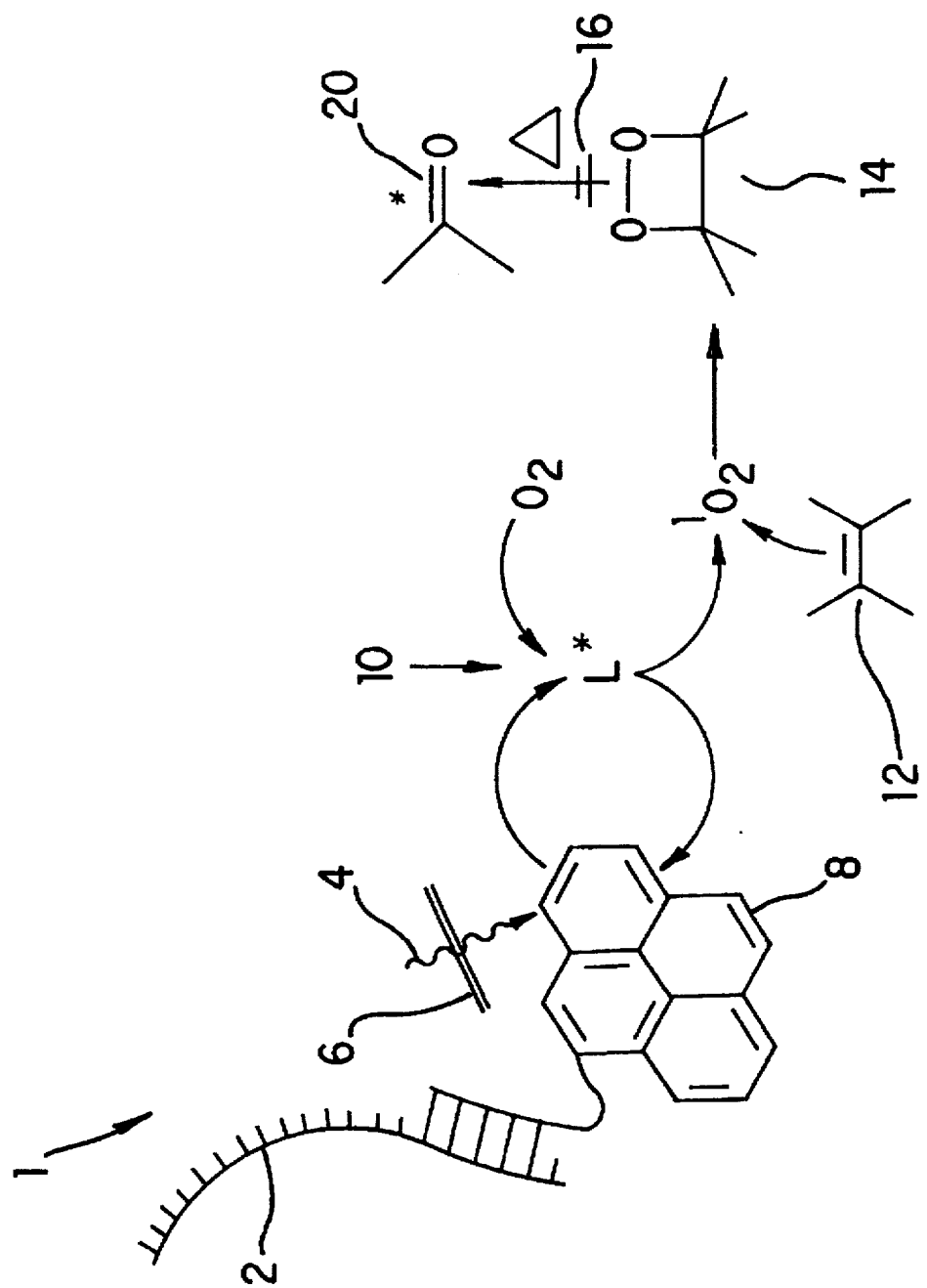
FIG. 1 shows the use of a sensitizer with an olefin to produce a dioxetan which will emit light upon heating.

A scheme 1 for practicing the invention is set forth in FIG. 1. As shown there, naturalized DNA 2 is bound to the conjugate of pyrene sensitized-labeled oligonucleotide 8. Light 4 transmitted through a filter 6 to select the desired wavelength range, typically in the white light region, is used to excite sensitizer 8 to the triplet state. The excited triplet and molecular oxygen (ground state) react at 10 to form singlet oxygen, which is reacted with olefin 12 in excess to form dioxetane 14 which is accumulated. Dioxetane 14 is heated or chemically treated to release light which is transmitted through filter 16. The acridone 10 is formed in the excited state by the decomposition of dioxetane 14.

In practicing the present invention, specific binding materials are labeled with a sensitizer. Such sensitizers include without limitation essentially all the known dyes, including without limitation, methylene blue, rhodamine, perylene, aromatic hydrocarbons (e.g., pyrene), heterocyclic compounds, eosin, free porphyrins, metalloporphyrins, tetraphenylporphine, phthalocyanine, chlorins and various flavin derivatives each provided with a functionality that is complementary to the functionality of the specific binding material with which it is to be conjugated. Examples of specific sensitizers are set forth in "The Chemistry of Synthetic Dyes," Volumes I to IX, edited by K. Venkataraman (Academic Press, New York 1978), Handbook of Fluorescent and Research Chemicals, 5th Edition, 1992, by Richard P. Haugland, Molecular Probes, Inc., supra, and Schaap, supra. Essentially all dyes are capable of triplet state excitation, and hence, with few exceptions they are suitable when provided with a functional group of being used in the practice of this invention.

Particularly useful sensitizers include:

| Sensitizer | Singlet Oxygen Efficiency |
| --- | --- |
| Protoporphyrin dimethyl ester | 177.67 |
| Tetraphenylporphine | 40.33 |
| Methylpyrroporphine | 38.38 |
| Methylpyrroporphine ethyl ester | 53.13 |

-continued

| Sensitizer | Singlet Oxygen Efficiency |
|---|---|
| Protoporphyrin disodium salt | 72.81 |
| Co-Porphyrin | 40.19 |
| Hematoporphyrin | 6.72 |
| Phthalocyanine | 10.53 |

Sensitizers may be linked to specific binding material by methods which are well known in the art, including without limitation, by use of one or more functional groups chemically bound to the sensitizer that reacts with a complementary functional group associated with the specific binding material. Such technology is commonly employed for the bonding of dyes to specific bonding material using such functional groups as an N-hydroxysuccinimidyl ester linker reacting with a complementary amine, thiol or hydroxy linking group and incorporating the sensitizer via an amide, thiolester or ester group into a building block (e.g., a nucleotide or amino acid) of a specific binding material. The method of linking the sensitizer to the specific binding material will differ depending on the type of specific binding material and type of sensitizer used. Illustrative of suitable functional groups for coupling the sensitizer to the specific binding material are the following:

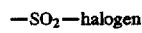

where R⁷ is the residue of an alcohol

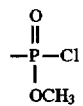

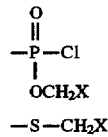
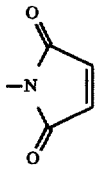

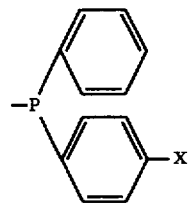
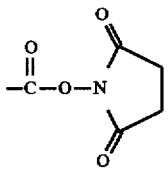

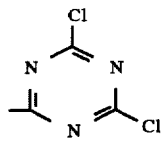
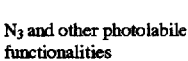

N₃ and other photolabile functionalities

where Y is halogen, i.e., Cl, Br, I and F.

In the foregoing illustrations, "X" is a functional halide such as chlorine, bromine and iodine. Functionality may be achieved by combining a functional group such as a carboxylic acid with a coupling agent such as dicyclohexyldicarbodiimide, 1-cyclohexyl-3-(2-morpholinoethyl)methyl-p-toluene sulphonate, N,N'-carbonyldiimidazole, $POCl_3$, $TiCl_4$, sulfuryl chloride fluoride $SO_2ClF$, chlorosulfonyl isocyanate, $P_2I_4$, pyridinium salts-$Bu_3N$, a mixture of tris(n-butyl)phosphine and $C_6H_6CNO$, and the like.

Illustrative of suitable sensitizers for the practice of this invention are the following compounds:

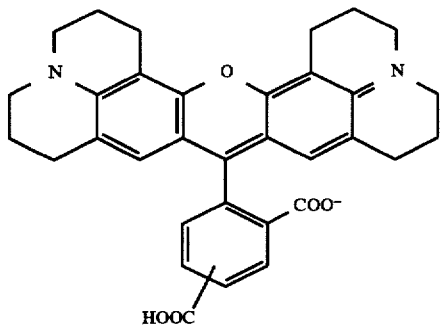

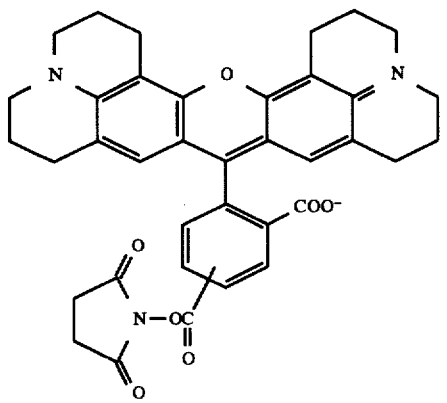

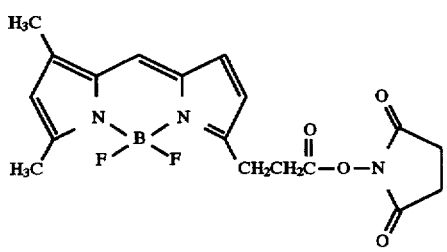

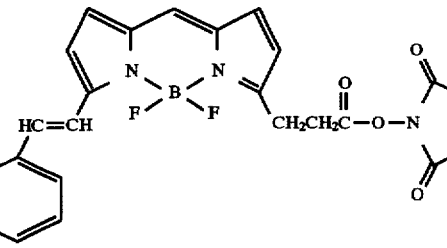

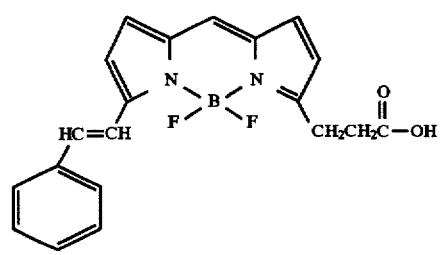

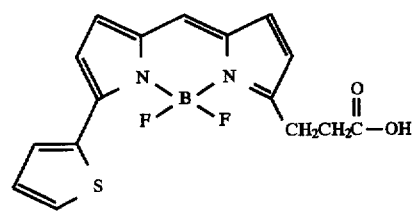
6
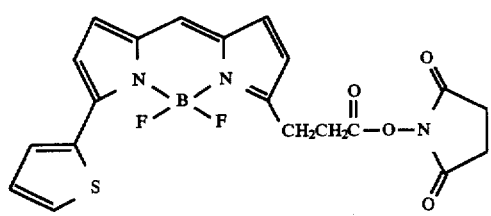
7
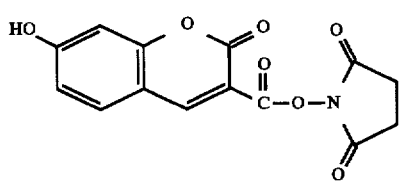
8
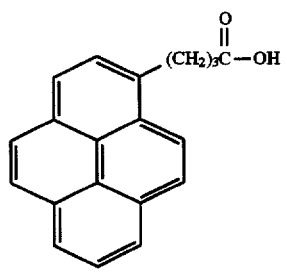
9
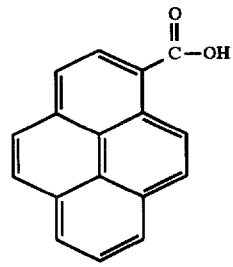
10
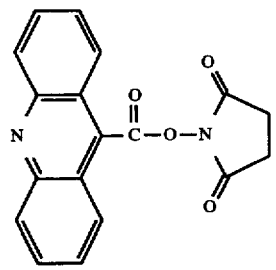
11
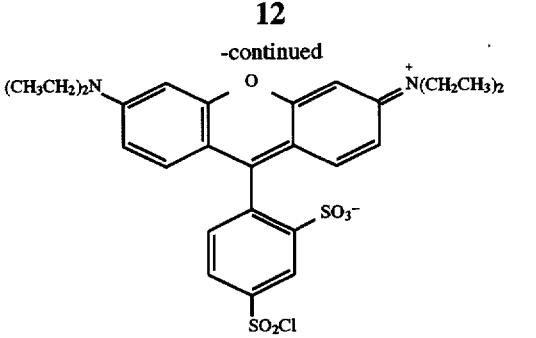
12
13
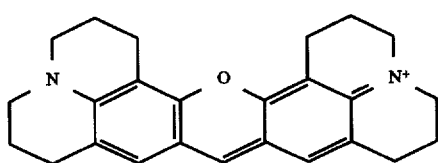
14
15
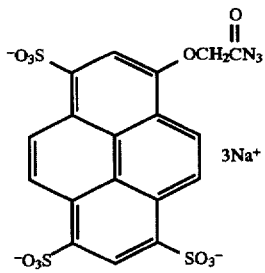
16
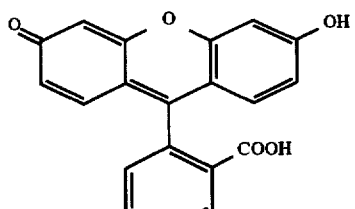
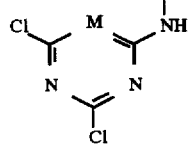
17
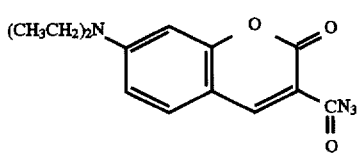

-continued

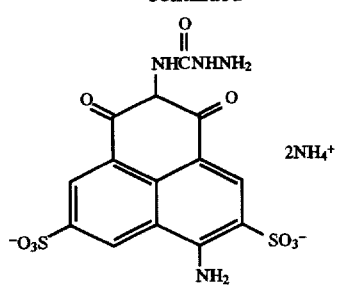
30
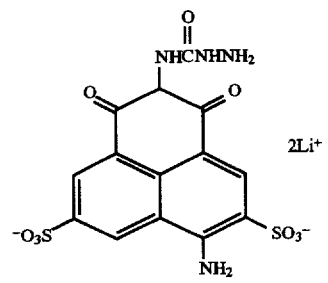
31
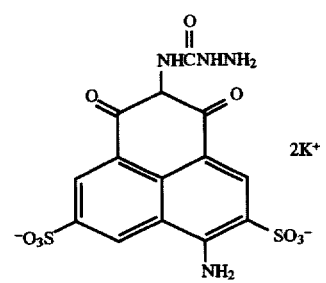
32
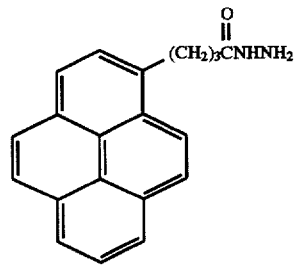
33
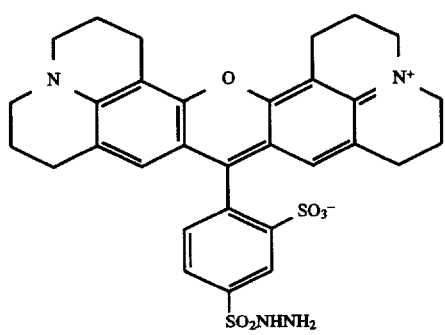
34
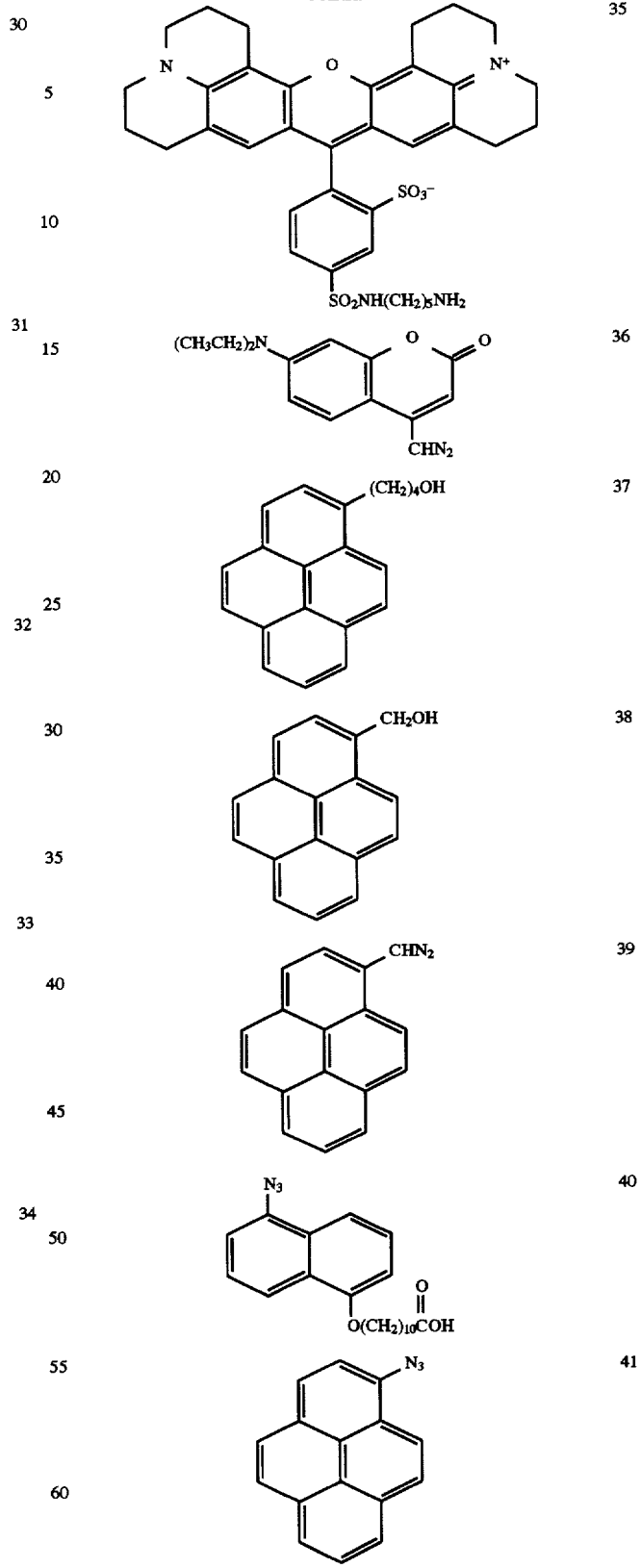

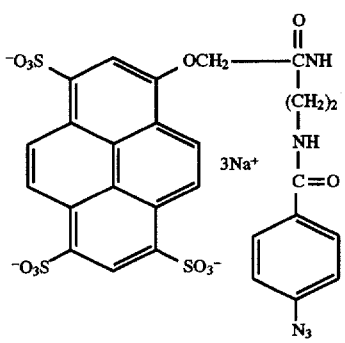
42
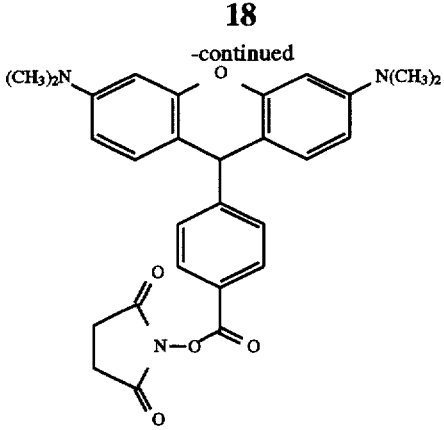
47
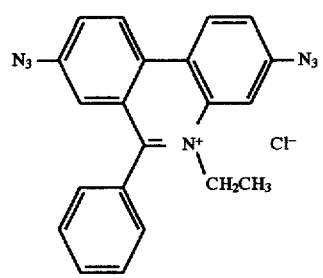
43
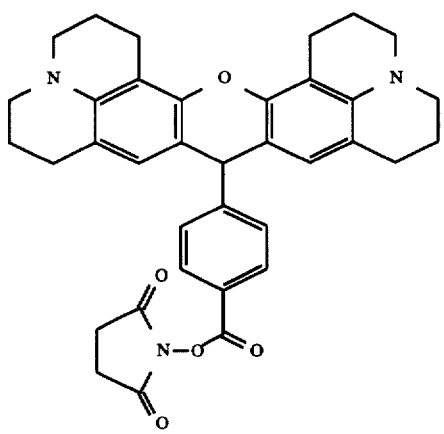
48
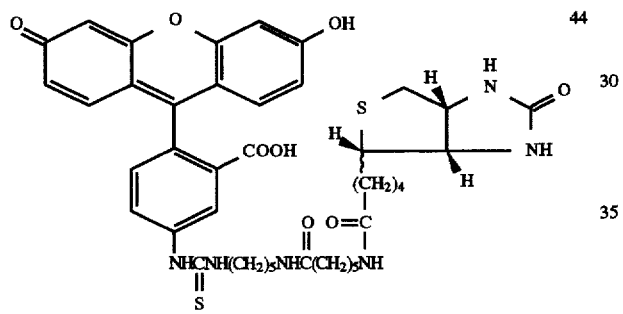
44
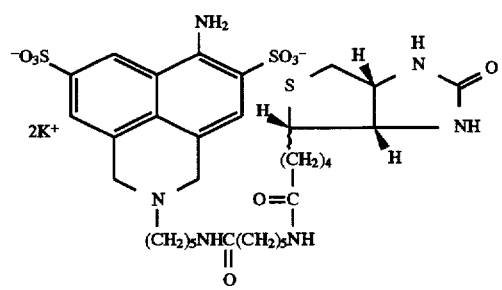
45
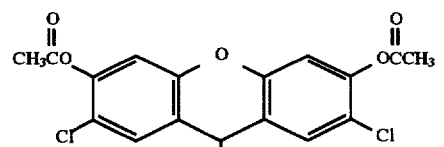
49
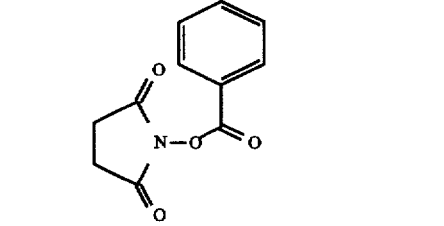
50
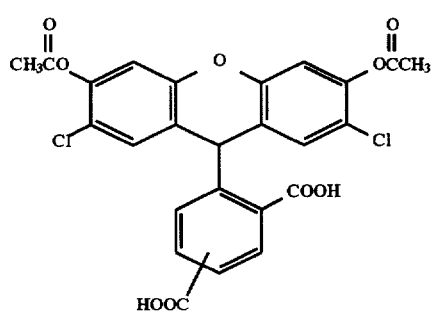
46
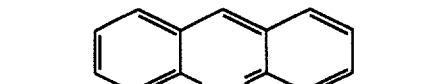
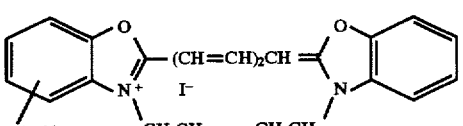
51
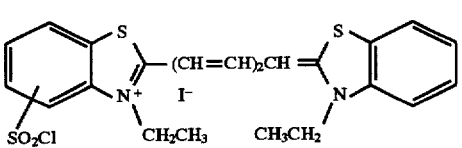
52

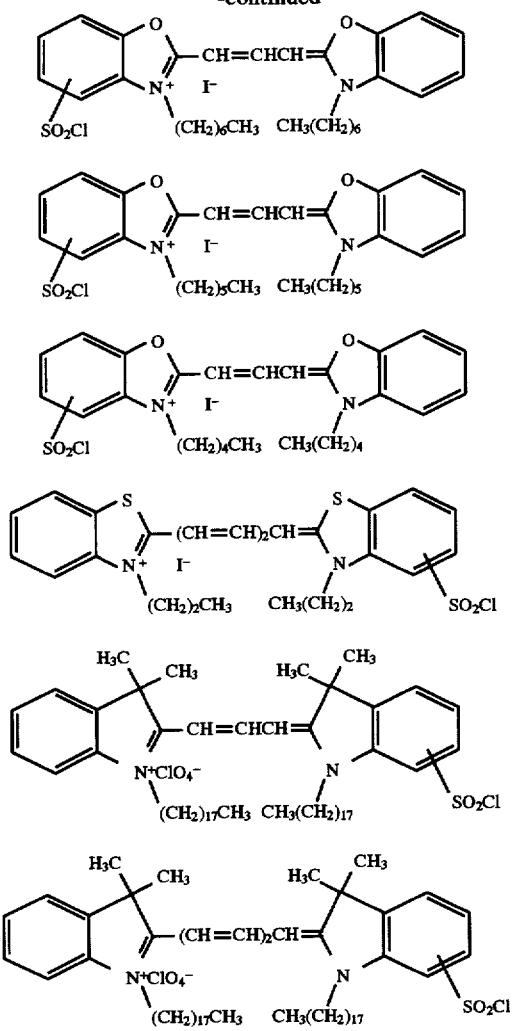
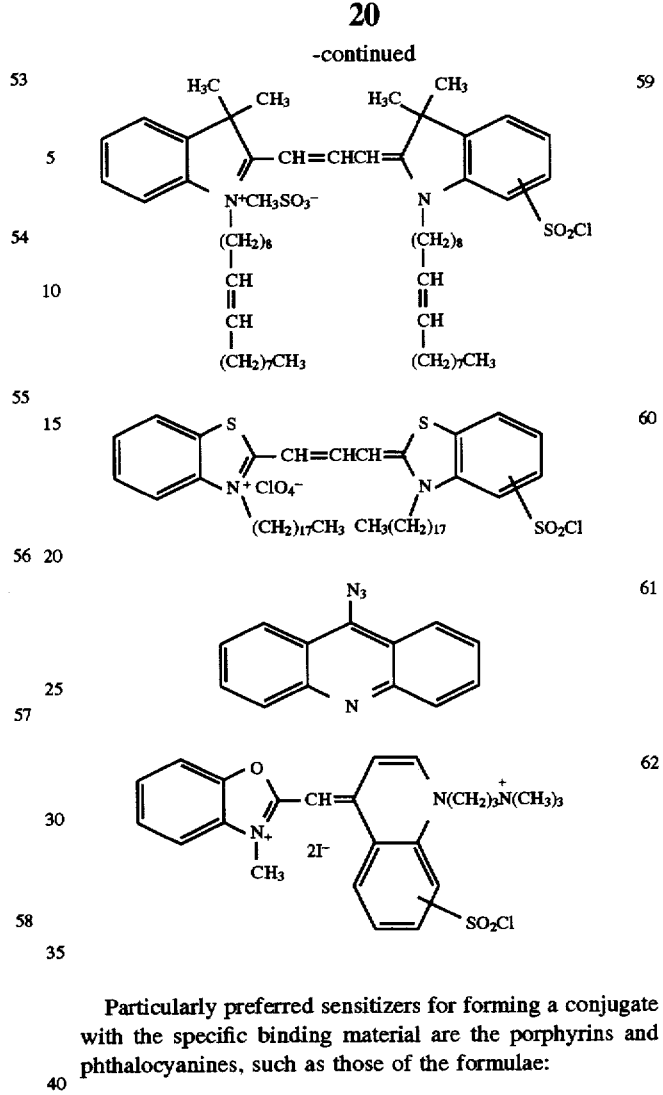
Particularly preferred sensitizers for forming a conjugate with the specific binding material are the porphyrins and phthalocyanines, such as those of the formulae:
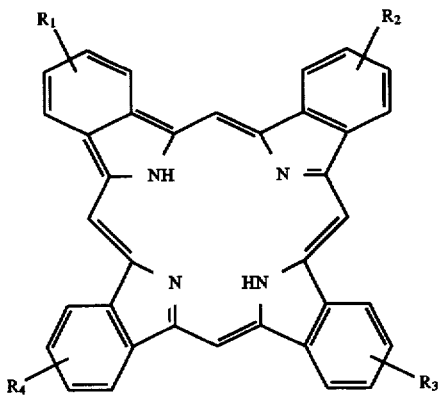

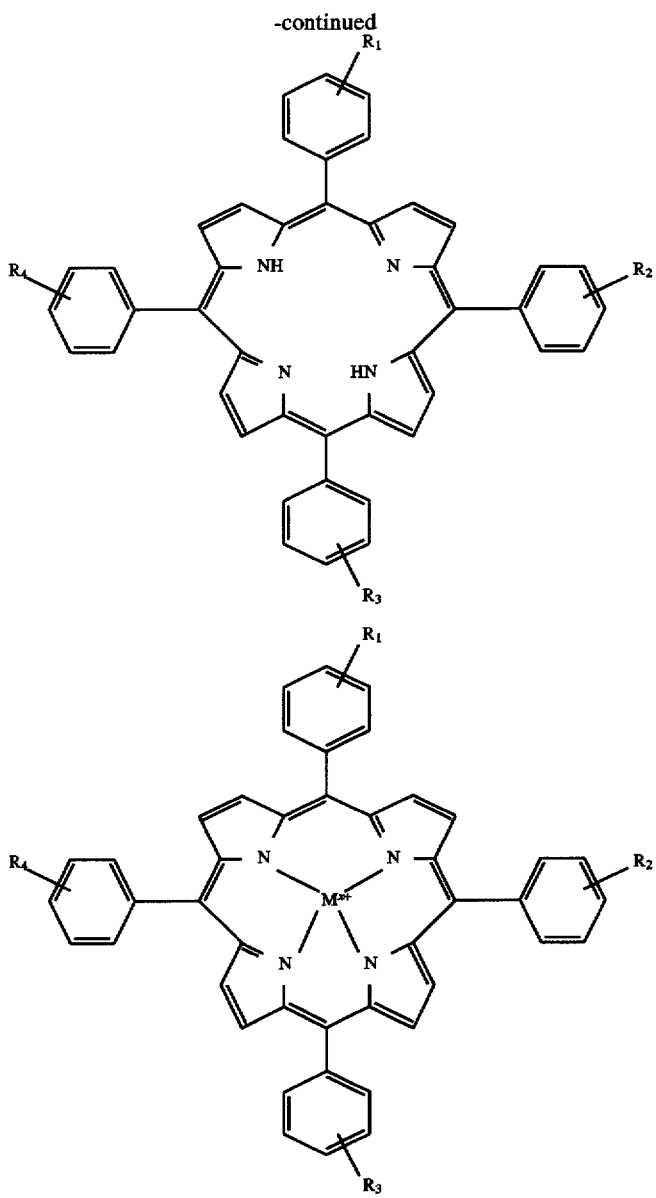

in which M is metal (such as aluminum, zinc, iron, copper and the like) having a valence of x, one or more of the R's are functional groups such as those depicted above, the more favorable functional group being sulfonyl chloride and N-hydroxysuccinimide. The remaining R's are hydrogen, alkyl (typically of 1 to about 6 carbon atoms), aryl, cycloaliphatic, and the like. Also desirable are the porphyrins of the formulae:

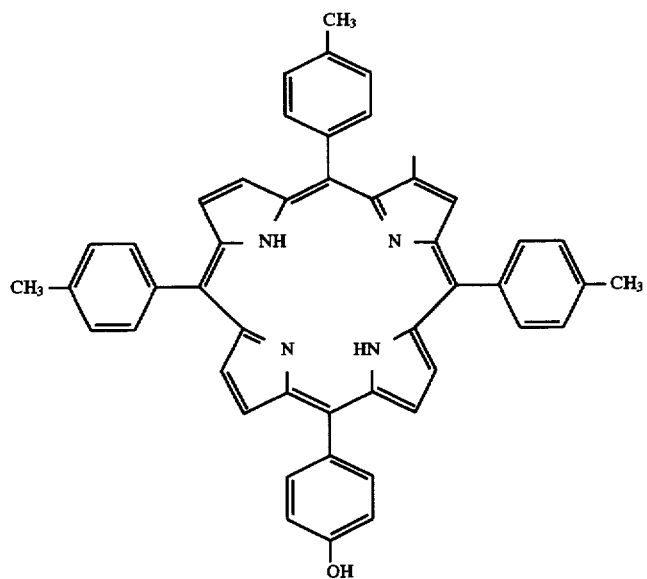
Mono(p-hydroxyphenyl
tri-(p-tolyl) porphyrin
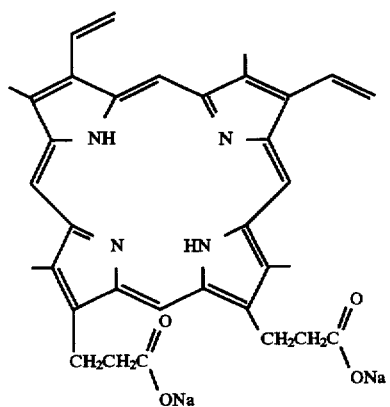
Protoporphyrin IX disodium salt
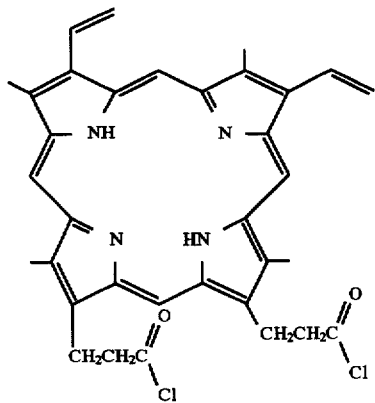
Protoporphyrin IX di-(acid chloride)

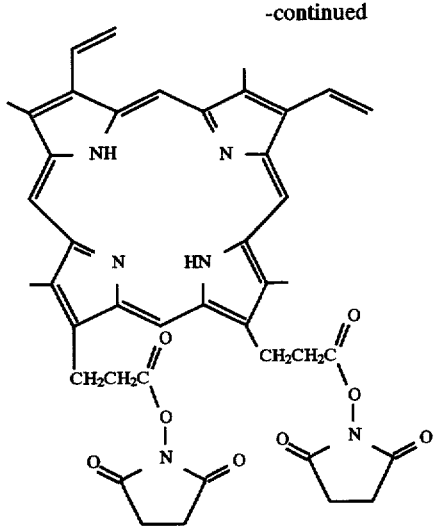

Protoporphyrin IX
di-(N-Hydroxysuccinimide)

In a preferred embodiment of the invention, it is desirable to substitute on the dye molecule sufficient water solubilizing groups so that the dye is more readily dispersed (from an aqueous dispersion to a solution) in water. Such groups include hydroxyl, alkyleneoxy, carboxyl, sulfonic, quaternary ammonium, and the like, directly attached to a carbon or chalcogen atom of or bonded to the dye molecule. Such substitutions are easily effected and standard procedures well known in the art are suitable for effecting such substitutions.

A specific binding material with the sensitizer attached (hereinafter "sensitizer conjugate") is useful in a broad range of specific binding assays for the presence of analyte in a sample by energizing the sensitizer to the triplet state. "Presence" in that context means the qualitative and/or quantitative detection of an analyte. Such assays may be directed at any analyte which may be detected by use of the sensitizer conjugate in conjunction with specific binding reactions. These assays include, without limitation, immunoassays, protein binding assays and nucleic acid hybridization assays.

In a typical immunoassay, the analyte is immunoreactive and its presence in a sample may be determined by virtue of its immunoreaction with an assay reagent. In a typical protein binding assay, the presence of analyte in a sample is determined by the specific binding reactivity of the analyte with an assay reagent where the reactivity is other than immunoreactivity. Examples of this include enzyme-substrate recognition and the binding affinity of avidin for biotin. In the typical nucleic acid hybridization assay, the presence of analyte in a sample is determined by a hybridization reaction of the analyte with an assay reagent. Analyte nucleic acid (usually present as double stranded DNA or RNA) is usually first converted to a single stranded form and immobilized onto a carrier (e.g., nitrocellulose, nylon paper). The analyte nucleic acid may alternatively be electrophoresed into a gel matrix. The immobilized analyte may then be hybridized (i.e., specifically bound) by a complementary sequence of nucleic acid. In the preferred practice of the invention, to minimize non-specific binding of the label, the membrane or filter should be blocked during prehybridization and hybridization with a known blocking agent, such as heparin, saponin, gelatin and non-fat dry milk powder. Heparin was the most preferred of the blocking agents tested. Data accumulated to date suggests that in general high concentrations of labeled probe generated a very rapid chemiluminescence signal on heating, usually less than twenty seconds, but with decreasing concentrations, the light emission profile extended over a longer period.

The foregoing specific binding assays may be performed in a wide variety of assay formats. These assay formats utilize a sensitizer conjugate which comprises the sensitizer attached to a specific binding material. "Specific binding material" means herein any material which will bind specifically by an immunoreaction, protein binding reaction, nucleic add hybridization reaction, and any other reaction in which the material reacts specifically with a restricted class of biological, biochemical or chemical species. In this category of assays, the sensitizer conjugate participates in a specific binding reaction and the presence of analyte in the sample is proportional to the formation of one or more specific binding reaction products containing the sensitizer conjugate. The assay is performed by allowing the requisite specific binding reactions to occur under suitable reaction conditions. The formation of specific binding reaction products containing the sensitizer conjugate is determined by measuring the signal produced as a result of the excitation of such products containing the sensitizer conjugate or by measuring the signal produced as a result of the excitatiion of unreacted or partially reacted sensitizer conjugate not contained in such products.

Typical assay formats are illustrated by sandwich assays, competitive assays, surface antigen assays, sequential saturation assays, competitive displacement assays and quenching assays.

In a typical sandwich format, the specific binding material to which the sensitizer is attached, is capable of specifically binding with the analyte. The assay further utilizes a reactant which is capable of specifically binding with the analyte to form a reactant-analyte-sensitizer conjugate complex. The reactant may be attached to a solid phase, including without limitation, dip sticks, beads, tubes, paper or polymer sheets. In such cases, the presence of analyte in a sample will be proportional to the signal produced as a result of the excitation of sensitizer bound to the solid phase after the specific binding reactions are completed. Such assay formats are discussed further in U.S. Pat. Nos. 4,652,533, 4,383,031, 4,380,580 and 4,226,993, which are incorporated herein by reference.

In a typical competitive format, the assay utilizes a reactant which is capable of specifically binding with the analyte to form an analyte-reactant complex and with the specific binding material, to which the sensitizer is attached, to form a sensitizer conjugate-reactant complex. The reactant may be attached to a solid phase, or alternatively reaction products containing the reactant may be precipitated by use of a second antibody or by other known means. In this competitive format, the presence of analyte is "proportional," i.e., inversely proportional, to the signal produced as a result of the excitation of sensitizer bound to the solid phase or precipitate. A further discussion of this assay format may be found in the immediately above mentioned U.S. patents.

In another assay format, the analyte may occur on or be bound to a larger biological, biochemical or chemical species. This type of format is illustrated by a surface antigen assay. In this format, the specific binding material is capable of specifically binding with the analyte and the presence of analyte is proportional to the analyte-sensitizer conjugate complex formed as a reaction product. This is illustrated by attaching the sensitizer moiety to an antibody which is specific to a surface antigen on a cell. The presence of the cell surface antigen will be indicated by the signal produced as a result of the excitation of sensitizer bound to the cells after the completion of the reaction. The cells themselves may be used in conjunction with a filtration system to separate the analyte-sensitizer conjugate complex which is formed on the surface of the cell from unreacted sensitizer conjugate. This is discussed further in U.S. Pat. No. 4,652,533.

The sensitizer moiety may be used in additional assay formats known in the art including without limitation sequential saturation and competitive displacement, both of which utilize a sensitizer conjugate where both (1) the specific binding material, to which the moiety is attached, and (2) the analyte specifically bind with a reactant. In the case of sequential saturation, the analyte is reacted with the reactant first, followed by a reaction of the sensitizer conjugate with remaining unreacted reactant. In the case of competitive displacement, the sensitizer conjugate competitively displaces analyte which has already bound to the reactant.

In a quenching format, the assay utilizes a reactant which is capable of specifically binding with the analyte to form an analyte-reactant complex and with the specific binding material, to which the sensitizer is attached, to form a sensitizer conjugate-reactant complex. A quenching moiety is attached to the reactant. When brought into close proximity to the sensitizer, the quenching moiety reduces or quenches the signal produced as a result of the excitation of bound sensitizer or reduces or quenches the transfer of electrons or energy from the excited sensitizer to an intermediate species (i.e., molecular oxygen or a leucodye). In this quenching format, the presence of analyte is proportional to the luminescence of the decaying dioxetans. A further discussion of this format may be found in U.S. Pat. Nos. 4,220,450 and 4,277,437, which are incorporated herein by reference.

In consideration of the above discussed assay formats, and in the formats to be discussed below, the order in which assay reagents are added and reacted may vary widely as is well known in the art. For example, in a sandwich assay, the reactant bound to a solid phase may be reacted with an analyte contained in a sample and after this reaction the solid phase containing complexed analyte may be separated from the remaining sample. After this separation step, the sensitizer conjugate may be reacted with the complex on the solid phase. Alternatively, the solid phase, sample and sensitizer conjugate may be added together simultaneously and reacted prior to separation. As a still further but less preferred alternative, the analyte in the sample and the sensitizer conjugate may be reacted prior to addition of the reactant on the solid phase. Similar variations in the mixing and reaction steps are possible for competitive assay formats as well as other formats known in the art. "Allowing under suitable conditions substantial formation" of specific binding reaction products shall herein include the many different variations on the order of addition and reaction of assay reagents.

In the second category of assay formats, the assay utilizes an unconjugated improved sensitizer compound. The presence of analyte in the sample is proportional to the formation of one or more specific binding reaction products which do not themselves contain the sensitizer moiety. Instead, the sensitizer compound chemiluminesces in proportion to the formation of such reaction products.

The assays described above may be heterogeneous or homogeneous. In heterogeneous assays, the reaction products, whose formation is proportional to the presence of analyte in the sample, are separated from other products of the reaction. Separation can be achieved by any means, including without limitation, separation of a liquid phase from a solid phase by filtration, microfiltration, double antibody precipitation, centrifugation, size exclusion chromatography, removal of a solid phase (e.g., a dip stick) from a sample solution or electrophoresis. For example, in a sandwich assay the reactant-analyte-sensitizer conjugate complex is separated from unreacted sensitizer conjugate. In a surface antigen assay, the analyte-sensitizer conjugate complex is separated form unreacted sensitizer conjugate. In a competitive assay, the reactant-sensitizer conjugate complex is separated from unreacted sensitizer conjugate. In a sequential saturation assay and in a competitive displacement assay, the reactant-sensitizer conjugate complex is separated from unreacted sensitizer conjugate. Alternatively, in homogeneous assays the reaction products are not separated. After the assay reagents have been allowed to react, the signal may be measured from the whole assay mixture whether such mixture is in solution, on a solid phase or distributed between various membrane layers of a dip stick or other solid support. The quenching assay illustrates a more complex homogeneous assay in which separation is unnecessary. It is contemplated that either category of assay formats may give rise to either heterogeneous or homogeneous formats.

Another example of a homogeneous assay is illustrated by European Patent Application number 823 03699.1, published Oct. 16, 1985 (Pub. No. 070 685), which is incorporated by reference. In this publication, a homogeneous hybridization assay is disclosed where two probes are used where one is labeled with a sensitizer moiety and the other is labeled with an absorber/emitter moiety. The assay can be carried out in solution without the need of any immobilization procedures. In the present invention, two strands of DNA are preferably selected which read from opposite ends. One strand is preferably labeled with a sensitizer moiety whose excited state produces a high fluorescence quantum yield. The other strand is preferably labeled with a sensitizer which is excited by the other label. Alternatively, the sensitizer moiety could be replaced by a heavy atom (I or Br)

containing compound, which would by Intersystem crossing, transform the sensitizer label on the second strand from a weak to a strong sensitizer when such heavy atom containing compound is in close proximity to the sensitizer label.

In addition to the foregoing, sensitizer labels may be used for DNA sequencing. In existing sequencing of DNA, four different fluorescent dyes are used, one for each of the reactions to A, T, C and G. In the present invention, four sensitizers each having a different excitation wavelength may be used in conjunction with four filters to sequentially excite the appropriate sensitizer.

In assays utilizing a sensitizer conjugate, the presence of analyte may be detected by excitation of the sensitizer with the appropriate radiation or other stimulus (e.g., electron transfer, electrolysis, electroluminescence or energy transfer). The excited sensitizer will then react with an "intermediary species" (e.g., molecular oxygen or a leucodye). The resulting products and further reactions depend on which intermediary species is employed.

When molecular oxygen is the intermediary species, singlet molecular oxygen is produced and the sensitizer returns to its original unexcited state. The singlet molecular oxygen will then react with an olefin to form either a dioxetan or a peroxide. An olefin is characterized by the general formula:

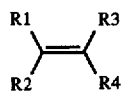

wherein R1, R2, R3 and R4 are any group. R1, R2, R3 and/or R4 can in some instances be joined to each other to form ring or ring-like structures as, for example, in structures (1) and (4) below:

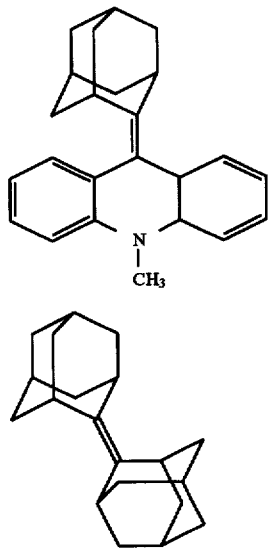

(1)

(4)

The character of the carbon atom within each of R1, R2, R3 and R4 which is closest to the double bond (the "adjacent carbon") in a given olefin will determine whether a dioxetan or a peroxide will form upon the reaction of the olefin with singlet molecular oxygen. If all of the adjacent carbons are (a) a bridgehead or (b) bear no hydrogen atoms, a dioxetan will be formed. For example,

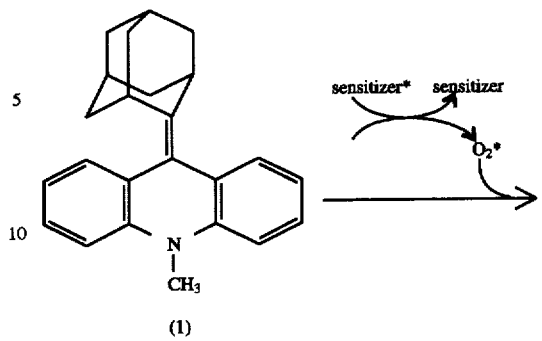

(1)

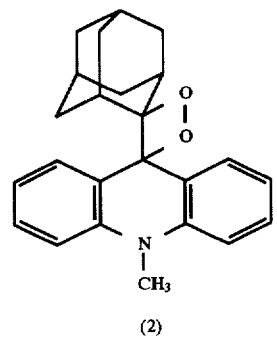

(2)

Upon heating, the dioxetan decays producing a detectable photon. For example:

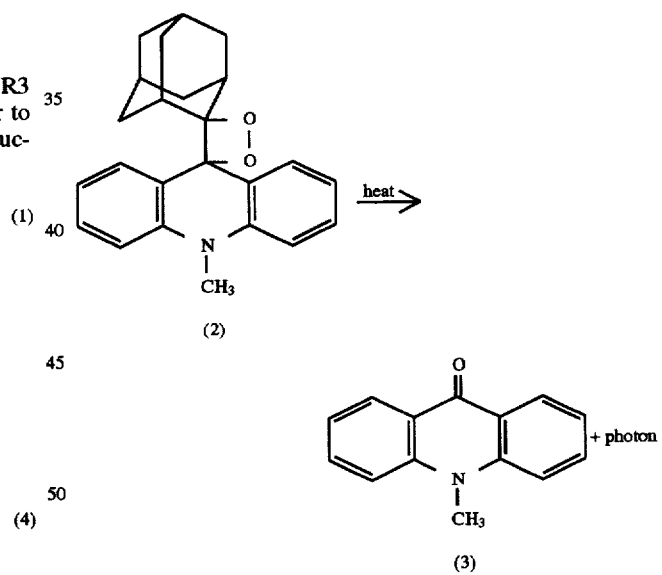

(1)

(2)

(3)

Substituted olefins which have electron donating groups among their substitutions are preferred for practicing the present invention because they produce dioxetans with increased quantum yield upon decay. Preferably, R1 and R2 and/or R3 and R4 are joined to form a ringed moiety which is fluorescent. For example, in structure (1) above, R1 and R2 form a N-methyl acridan. Having a fluorescent moiety "on one end" of the olefin will lead to an additional increase in quantum yield from the resulting dioxetan.

If one or more of the adjacent carbons is (a) not a bridgehead and (b) bears at least one hydrogen atom, a peroxide will be formed. Upon heating the peroxide will also decay to produce a detectable (although weak) emission of photons. Alternatively, the peroxide can be used to oxidize a chromogen to produce a detectable color change or fluorescence.

Illustrative olefins suitable for the practice of the invention include the following:

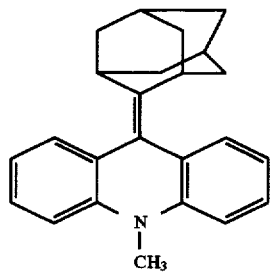

9-Adamantylidene-
N-methylacridan

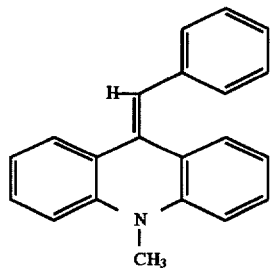

9-Benzylidene-
10-methylacridan

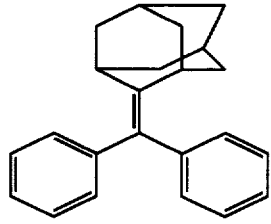

2-Diphenyl methylene
adamantane

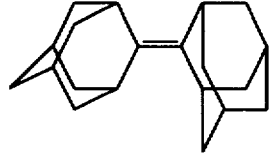

Adamantylidene
Adamantane

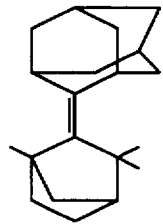

9-Adamantane
Fenchane

-continued

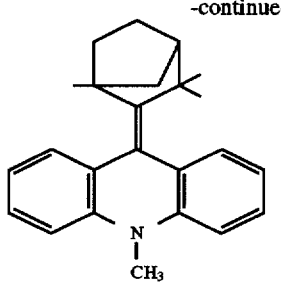

9-Fenchylidene-
N-methyl acridan

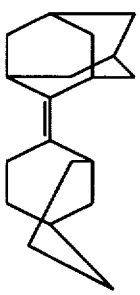

9-Adamantylidene bicyclo [3.3.1] nonane

In addition to triggering the light reaction by heating the accumulated dioxetane, a protected form of the dioxetane is contemplated by the invention so that it is stable until the protecting group is removed chemically, and light is emitted during the subsequent decomposition of the now unstable dioxetane. Illustrative of olefins containing such protected groups suitable for forming the stable dioxetanes until the protected groups are removed include the following:

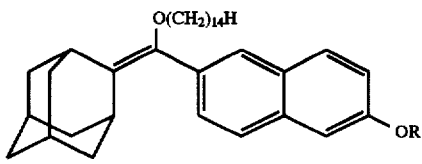

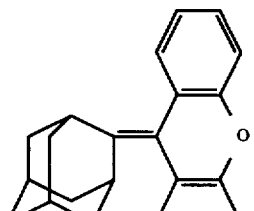

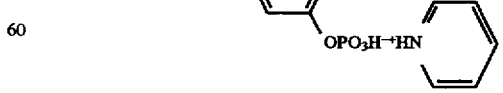

In the above, R may be hydrogen and acyl of 2 to about 8 carbon atoms, such as acetyl, proprionyl, and the like. Such class of olefins and their conversion to dioxetanes are illustrated in Schaap et al., *Tetrahedron Letters*, Vol. 28, nos.

9 and 11, pp. 935–938 and 1159–1162, respectively, 1987, Pergamon Journals Ltd., Great Britain. The reaction sequence may be illustrated by the following:

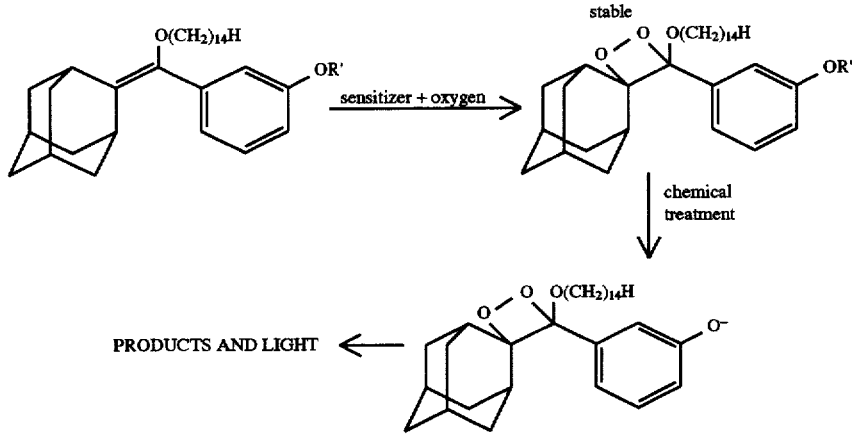

In the above structures, R' may be H, and the triggering chemical mechanism is the raising of the pH, phosphate, and the triggering chemical mechanism is by the addition of the enzyme alkaline phosphatase, or ester, and the triggering mechanism is the addition of the enzyme esterase or by acid or alkaline hydrolysis.

When a leucodye is the intermediary species, the excited sensitizer is reduced by the leucodye. The oxidized leucodye becomes visible and is detectable by the resulting color change or fluorescence. The reduced sensitizer will react with singlet oxygen to produce hydrogen peroxide and return the sensitizer to its original unexcited state. The hydrogen peroxide can be used to oxidize a chromogen to produce a detectable color change or fluorescence or to oxidize a sensitizer moiety to produce a detectable photon. Leucodyes are dyes (e.g., hydroxyanthraquinones and methylene blue) which are colorless in their reduced forms and become colored upon oxidation. Examples of leucodyes are set forth in "The Chemistry of Synthetic Dyes," Volumes I to IX. edited by K. Venkataraman (Academic Press, New York 1978), and "Singlet Molecular Oxygen," edited by A. Paul Schaap, supra, which are incorporated in their entirety herein by reference thereto. The leucodyes can be oxidized by singlet molecular oxygen as described by Kautsky et al, supra, p. 33 (see Schaap, "Singlet Molecular Oxygen").

Since the amount of sensitizer being stimulated is correlatable to the presence of analyte, the signal (i.e., photon or color change or fluorescence) produced by the reactions discussed above can also be correlated to the presence or amount of analyte in the sample.

"Chromogens" which produce a color change or fluorescence upon oxidation with peroxides are well known in the art. Suitable "chromogens" which produce a color change include without limitation benzidine and derivatives of benzidine. Suitable "chromogens" which produce fluorescence include without limitation fluorescin (i.e., dihydrofluorescein) and derivatives thereof. "Allowing under suitable conditions" shall include without limitation, where relevant, the act of separating those specific binding reaction products (the formation of which are proportional to the presence of analyte in the sample, from other reaction products), exciting the sensitizer conjugate contained in any specific binding reaction product, adding other reagents (i.e., olefin, leucodye, chromogen or chemiluminescent moiety), and/or heating the dioxetan or peroxide to induce decay, measuring a color change or fluorescence by any means (e.g., visually, by absorbence, by reflectance, by fluorescence).

EXAMPLE 1

To form a sensitizer conjugate, pyrenebutyric acid was attached to the 5' terminal phosphate of a kinased synthetic oligonucleotide (20 bases; sequence: 5'-TTCAATCATGCGAAACGATC-3') via a hexanediamine linker as shown below:

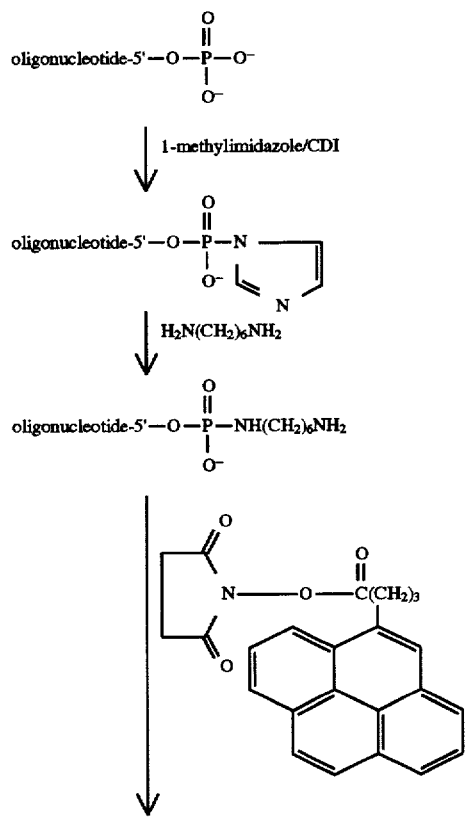

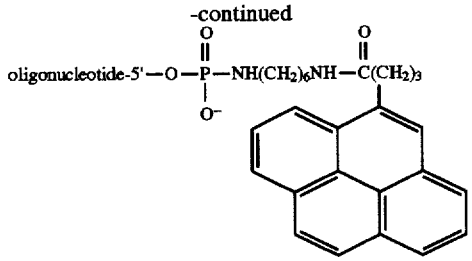

The oligonucleotide was synthesized on an automated synthesizer (commercially available from Applied Biosystems, Foster City, Calif. 94404, Model 380B).

The oligonucleotide (2.5 μg) was converted to the 5'-phosphorimidazolide by treatment with 0.1M 1-ethyl-3,3-dimethylaminopropyl carbodiimide (CDI) in 0.1M 1-methyl imidazole buffer at pH 7.8 for one hour at room temperature with vigorous shaking. The product was converted to the 5'-hexanediamine adduct by treatment with 0.25M hexanediamine at pH 7.8 for one hour at 50 C.

The pyrene (sensitizer)-labeled oligonucleotide was formed by reacting the 5'-hexanediamine adduct with 0.25M pyrenebutyric acid as its N-hydroxysuccinimidyl ester in 1-methyl-imidazole buffer at pH 7.8 at room temperature.

The olefin 9-(adamantylidene)-N-methyl acridan [structure (1) above] was synthesized as follows. N-methyl acridan (15.2 g, 0.074 moles) and phosphorous pentasulfide (10.3 g, 0.046 moles) were mixed in dry pyridine (470 ml) and refluxed for 1 hour. Red crystals were collected after cooling the solution. Recrystallization from xylene gave 12.5 g of N-methyl acridimethione.

Adamantanone-p-tolylhydrazone and triphenylphosphine in dimethylacetamide (DMA) were added to dry sodium hydride and the mixture was heated to 120° C. for 20 minutes. N-methyl acridimethione was added to the reaction mixture and the new mixture was refluxed for 2 hours. The solution was cooled and the collected solids were recrystallized from xylene. The resulting product was chromatographed on silica gel eluted with toluene. The first fraction ($R_f$ 0.8) was collected. The toluene was evaporated and the resulting 9-(adamantylidene)-N-methyl acridan was recrystallized from acetone.

In performing a nucleic acid hybridization assay, DNA was immobilized on nylon filters (commercially available as Hybond from Amersham, U.K.) by methods known in the art. A complementary oligonucleotide ("Someo") and a noncomplementary (i.e., control) oligonucleotide ("pAT 153") were used as targets in a standard Southern blot procedure using the sensitizer-labeled oligonucleotide as the probe. Target oligonucleotides were assayed at 0.2 μg, 0.02 μg and 0.002 μg concentrations. The sample was concentrated in a 2×2 cm spot. Hybridization was carried out with 200 μg/ml of sensitizer-labeled oligonucleotide at 37° C. for 2 hours in hybridization buffer (6× SSC, 0.5% SDS, 110× Denhardts) and washing was performed in the usual manner.

After hybridization and washing were complete, 50 μl 1×10$^{-6}$M 9-(adamantylidene)-N-methyl acridan in dichlorotoluene was added to each hybridization spot. Each spot was irradiated with an ultraviolet source (150 W xenon arc lamp) for 10 minutes in the presence of ambient molecular oxygen. Half of the spots were also heated to 100° C. immediately after irradiation to induce decay of the dioxetan formed upon irradiation.

The luminescence of the decaying dioxetans was measured using a photomultiplier tube (commercially available from Thorn EMI, type 9813 QB) which was held at 0° C. in a standard thermoelectrically cooled housing. Samples to be measured were placed inside a light tight chamber on a heating block. A thermocouple mounted inside the heating platen allowed temperature control (±0.1° C. within the range of 30°–300° C.) of the heating elements directly below the heating platen. The sample cell was also hermetically sealed to allow measurement to occur under the desired atmosphere.

The resulting luminescent measurements are summarized in Tables 1 and 2.

TABLE 1

Luminescence at Room Temperature

| Concentration[b] | Luminescence[a] | |
| --- | --- | --- |
| | Someo | pAT 153 |
| 0.2 μg | 9.5845 | 5.7100 |
| 0.02 μg | 8.8377 | 8.5845 |
| 0.002 μg | 16.450 | 17.151 |

[a]counts × 102; background (procedure without using probe) 5.6092 × 102
[b]of target oligonucleotide

TABLE 2

Luminescence at 100° C.

| Concentration[b] | Luminescence[a] | |
| --- | --- | --- |
| | Someo | pAT 153 |
| 0.2 μg | 6253.5 | 498.57 |
| 0.02 μg | 23.905 | 17.023 |
| 0.002 μg | 658.14 | 136.08 |

[a]counts × 102; background (procedure without using probe) 14.933 × 102
[b]of target oligonucleotide Although the data were produced by a crude and unrefined assay protocol, in each instance, heating produced a stronger signal and the complementary target produced more counts than the control target. Ways of refining this assay procedure (e.g., better washing away of each type of reagent, addition of inhibitors to reduce autoxidation of the olefin, use of more effective sensitizers, use of filters appropriate to the primary wavelength absorbed by the sensitizer, cooling the spot while it is irradiated, regulating and/or optimizing the rate of heating, use of more reactive olefins, use of olefins giving higher light-yielding dioxetans and use of solvents to promote migration of singlet oxygen) will be readily recognized by those skilled in the art.

EXAMPLE 2

The probe assay from the preceding example may be used with porphyrin labeled oligonucleotides. The porphyrin (sensitizer)-labeled oligonucleotide may be formed using $N^6$-(6-Aminohexyl)dATP (hereinafter "AHdATP") shown below:

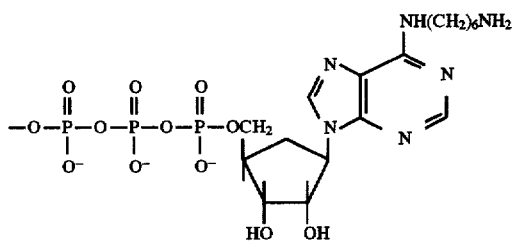

DNA is subjected to a nick translation in known ways in the presence of AHdATP to form strands of DNA having exposed —NH₂ functional groups. This product is reacted with NHS ester-porphyrin conjugate in the presence of DMF/H₂O in known ways to form strands of DNA having attached

Protoporphyrin IX di-(Acid Chloride)

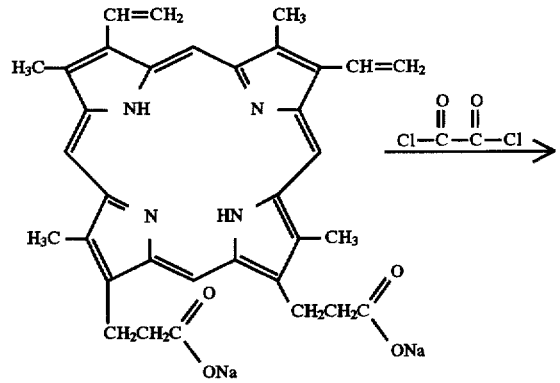

Protoporphyrin IX disodium salt (0.3 g, 0.5 mm) was suspended in 20 ml of dry dichloromethane. Oxalyl chloride (0.5 ml, 3.9 mM) was carefully added in three aliquots, and the mixture stirred for 18 hours at room temperature. The excess oxalyl chloride was removed under vacuum, the residue washed twice with 50 ml of dichloromethane and dried under vacuum. Purple needles in almost quantitative yield with a melting point >300° C., were recovered and used in the next stage of the reaction without further purification.

T.L.C.
Rf (acetonitrile): 0.96, 0.82 (main spot).
Protoporphyrin IX di-(N-Hydroxysuccinimide)

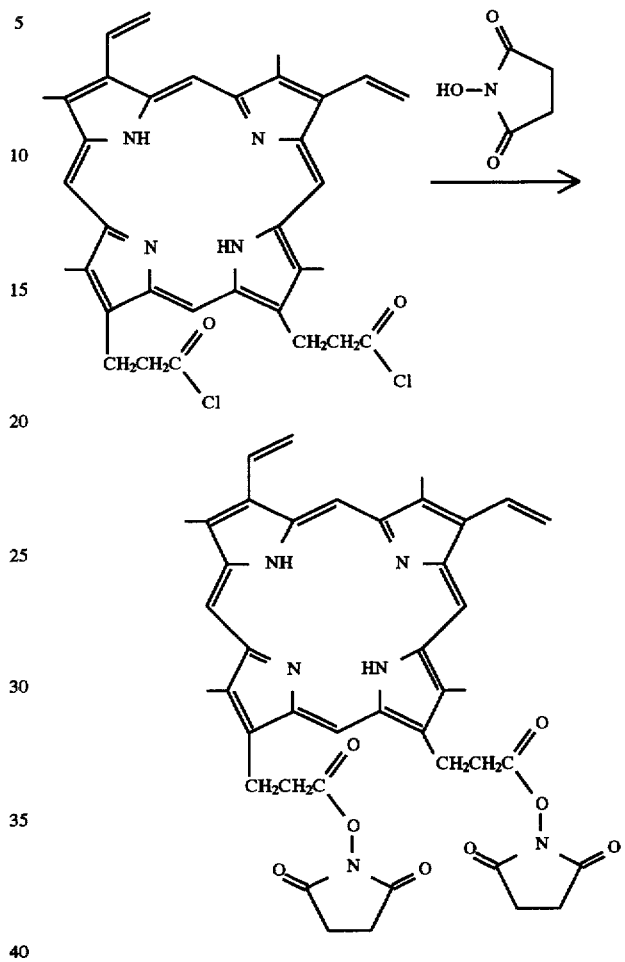

Protoporphyrin IX di-acid chloride (0.3 g, 0.5 mm) and N-hydroxysuccinimide (0.1 g, 0.9 mM) in dichloromethane (30 ml) were stirred for 48 hours at room temperature. The mixture was then refluxed for 2 hours and the solvent evaporated under vacuum. Unreacted N-hydroxysuccimide was removed by crystallization in chloroform. Analytical T.L.C indicated several components, and consequently applied to a very short silica gel column and using chloroform as the eluent. The first fraction was collected $R_f$ (chloroform) 0.73, and the solvent evaporated. Crystallization from chloroform/petroleum ether (3:2) gave red brown crystals in 47% yield (0.18 g). M.P. 121°–123° C. IR (Nujol) 1818, 1 (succinimidyl,C=O), 1742 (ester, C=O); UV (in CHCl₃) 268 nm (3.37), 407 (5.22), 507 (4.17), 541 (4.06), 578 (3.87), 632 (3–75), and 669 (3.67); ¹H-NMR (CDCl₃) δ9.80–9.42 (m, methine H's, 4H) δ8.05–7.18 (m, vinyl H's, 2H) δ6.39–5.98 (m, vinyl H's,4H) δ4.17–2.51 (m, aromatic CH₃, CH₂CH₂ C=O, CH₂—CH₂, 28H).

Detection of Human Burkitt's Lymphoma DNA
Using Chemiluminescence Hybridization Probes The following illustrates the clinical application of the invention in the detection and diagnosis of a genetic disease. The target DNA was obtained from the lymph node of a patient with Burkitt's lymphoma (0.5 µg/ml). Probe 1: CH-ras DNA fragment, and Probe 2: C-myc DNA fragment. Target DNA was serially diluted (concentration range 100 ng to 0.001 ng), blotted on nylon membrane and baked for 4 hours at 85° C.

| Prime Label Protocol | |
|---|---|
| DNA fragment (Probe 1 or 2) | 11 µl |
| Oligo-labelling buffer | 4 µl |
| BSA (10 mg/ml) | 1 µl |
| [α-$^{32}$P]-dCTP 800 Ci/mmol | 3 µl |
| Klenow enzyme | 1 µl |
| AHdATP linker, 0.4 mM | 10 µl |

Oligo-labelling buffer was prepared according to literature methods without dATP and dCTP bases. The reaction cocktail was incubated for 4 hours at room temperature. Protoporphyrin IX di-NHS (5 µl 10$^{-7}$ Min) in dimethylformamide (DMF) was added and the reaction mixture incubated for a further 4 hours at room temperature. A 60% incorporation of labels was observed. The labeled probe was denatured by the addition of 70 µl TE, 30 µl 2M NaOH and 100 µl tris buffer, and purified by gel exclusion chromatography. The labeled probe was added to the plastic bag containing the prehybridised (4 hours at 42° C.) target DNA with 20 mg/ml heparin as the blocking agent. Hybridization was carried out at 42° C. overnight. Unbound probe molecules were removed by washing in 250 ml solutions of 5× SSC, 0.1% SDS and 1× SSC, 0.1% SDS. Further washing was required as a result of high background observed on the autoradiograph. 1× SSC, 0.1% SDS; 0.1× SSC, 0.1 SDS and 0.1× SSC, 0.1% SDS, 20% CH$_3$CN, and 0.1% BHT. Each washing was performed for 30 mins. at 42° C. The hybridized probe was autoradiographed overnight at −70° C. The dot blot was cut out and monitored using a photon counting apparatus similar to that described previously. After hybridization and washing were complete, 10 µl 1×10$^{-6}$M 9-(adamantylidene)-N-methyl acridan

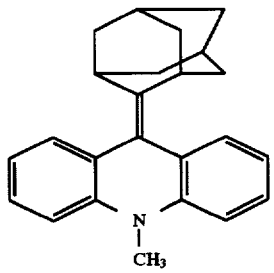

9-Adamantylidene N-methyl acridan in acetonitrile with BHT in dichlorotoluene was added to each hybridization spot. Each spot was irradiated with an ultraviolet source (150 W xenon arc lamp) at 1.3 kV for 2 minutes using a dark yellow filter in the presence of ambient molecular oxygen. Half of the spots were also heated at 200° C. immediately after irradiation to induce decay of the dioxetan formed upon irradation. The chemiluminescent results were:

| DNA Concentration/ng | Average Peak Luminescence/× 10$^6$ | Average Area/× 10$^8$ |
|---|---|---|
| As To Probe 2 (c-myc DNA fragment) | | |
| 100 | 5.53 | 2.74 |
| 10 | 5.41 | 1.81 |
| 1 | 5.28 | 1.63 |

| DNA Concentration/ng | Average Peak Luminescence/× 10$^6$ | Average Area/× 10$^8$ |
|---|---|---|
| 0.1 | 5.06 | 1.51 |
| 0.001 | 4.80 | 1.27 |
| Blank | 4.61 | 1.21 |
| 100 | 5.48 | 2.15 |
| 10 | 5.47 | 1.60 |
| 1 | 5.42 | 1.46 |
| 0.1 | 5.40 | 1.36 |
| 0.01 | 5.34 | 1.14 |
| 0.001 | 5.05 | 1.05 |
| Blank | 4.94 | 1.18 |
| As to Probe 1 (CE-ras DNA fragment) | | |
| 100 | 0.97 | 0.38 |
| 10 | 0.98 | 0.42 |
| 1 | 0.89 | 0.35 |
| 0.1 | 0.96 | 0.36 |
| 0.01 | 1.03 | 0.24 |
| 0.001 | 1.14 | 0.31 |
| Blank | 1.09 | 0.36 |

The data show sensitivity without any optimization of the procedure, was between 1 and 10 picogram. The c-myc DNA probe hybridized to the complementary DNA target and the ch-ras DNA fragment did not hybridize even though it was expected to do so. This was quantitatively confirmed by autoradiography. Chemiluminescence detection resulted in negligible light emission for the unhybridized ch-ras probe (acting as a control), giving confirmation of the selectivity, specificity and applicability of this non-radioactive format.

EXAMPLE 3

The probe assay from the preceding examples was repeated using protoporphyrin disodium salt as the label. Five microliters of DCTP, DGTP and dTTP (20 µM) were added to 1 µl test DNA (pUG), 3 µl (0.4 mM) AHdATP, and 10 µl H$_2$0. After brief mixing, 5 µl DNA Polymerase I was added. The mixture was then incubated at 15° C. for 60 minutes. DNA labeled with the aminohexyl group was then separated from unincorporated nucleotides by exclusion chromatography on Sephadex G-50 column eluting with 1×5 SC containing 0.1% SDS. Fractions were collected, followed by ethanol precipitation. After reaction according to Example 2 with NHS ester-protoporphyrin, the probe assay was performed according to Example 1. DNA was immobilized on nylon filters. Complementary oligonucleotide was used as a target in a standard Southern blot procedure using the sensitizer labeled oligonucleotide as the probe according to Example 1. The resulting spots were heated to 100° C. immediately after irradiation to induce decay of the dioxetan formed upon irradiation.

TABLE 3

| Luminescence At 100° C. For One Minute | | |
|---|---|---|
| Concentration of Target | First Assay Counts (Peak Height) | Second Assay Counts (Peak Height) |
| 100 µg | 1.58 | 2.67 |
| 10 µg | 1.02 | 1.65 |
| 1 µg | 0.69 | 1.03 |
| 0.1 µg | 0.49 | 0.88 |
| 0.01 µg | 0.37 | 0.74 |
| blank | 0.16 | 0.059 |

EXAMPLE 4

Example 3 was repeated using protoporphyrin disodium salt and $^{32}$P as simultaneous labels in order to compare the sensitivity of the assay using these two labels. One microliter of $^{32}$P-dCTP was added to the mixture of Example 3 prior to addition of 5 μl DNA Polymerase I. The assay was run against the following concentrations "A" of target DNA (keyed to the legends shown in FIG. 2):

| | |
|---|---|
| a | 100 μg |
| b | 10 μg |
| c | 1 μg |
| d | 0.1 μg |
| e | 0.01 μg |
| f | 0.005 μg |
| g | blank |

Figure 2:
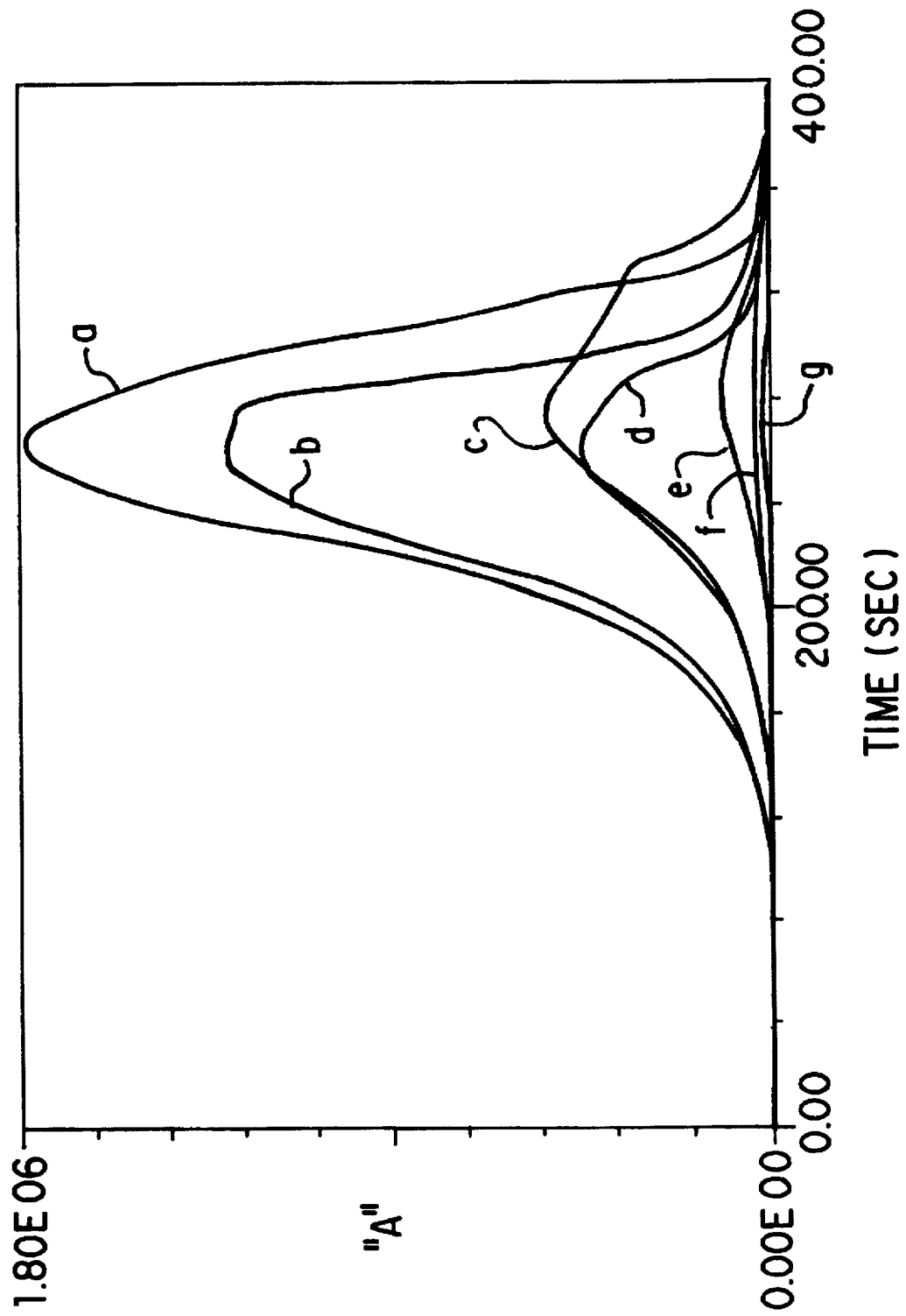
FIG. 2 shows the results of a probe assay for varying amounts of target DNA.

The results shown in FIG. 2 for heating the spots at 100° C. for 1 minute indicates a detection limit of 0.005 μg of target DNA in the above assay. Alternatively in the case of the $^{32}$P label, 24 hour exposure time in standard film detection system showed a comparable limit of detection.

Sensitizers may be selected for sensitivity to certain wavelengths which differ from the excitation wavelength for the background materials, including formation of generalized peroxides. For example, methylene blue or pyrene may be used as the sensitizer and an excitation filter may be incorporated so that only wavelengths which excite these sensitizers will result in singlet oxygen generation. Heating the membrane can generate background light from heating generalized peroxides. Triggering dioxetans with lower temperatures of decomposition will help lower background readings, especially where such temperatures are much lower than a temperature which generates background light. Finally, the olefin should be chosen to produce a dioxetan which emits at a different wavelength than the background. An emission filter can then be selected to reduce background. Excessive background can also be avoided by the use of chemical triggering, as described above, in which the dioxetane is formed in its protected form, with subsequent de-protection leading to light emission. These and other improvements should significantly increase the sensitivity of the sensitizer-labeled assays.

From the foregoing, it will be obvious to those skilled in the art that various modifications in the above-described methods, compositions and articles of manufacture can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, the scope of the invention being indicated by the appended claims rather than by the foregoing, and all changes which come within the meaning and range of equivalency of the claims are therefore intended to be embraced therein.

I claim:

1. A sensitizer conjugate comprising a sensitizer label attached to a specific binding material, that functions as a donor of energy, and an acceptor which uses that energy to evoke a detectable signal, in which the sensitizer label is a moiety that is induced to an excited state by radiation or by chemical or physical stimulus such that it is reactable with, and donates its energy to, (a) molecular oxygen to produce singlet molecular oxygen or (b) a leucodye to form a reduced form that is oxidizable to its original state by reaction with singlet oxygen thereby producing hydrogen peroxide, wherein the sensitizer is obtained by reacting the specific binding material with a porphyrin that has the formula:

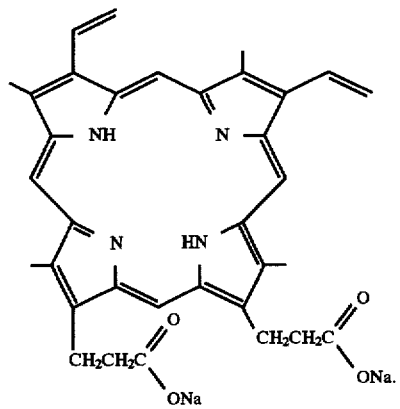

2. A sensitizer conjugate comprising a sensitizer label attached to a specific binding material, that functions as a donor of energy, and an acceptor which uses that energy to evoke a detectable signal, in which the sensitizer label is a moiety that is induced to an excited state by radiation or by chemical or physical stimulus such that it is reactable with, and donates its energy to, (a) molecular oxygen to produce singlet molecular oxygen or (b) a leucodye to form a reduced form that is oxidizable to its original state by reaction with singlet oxygen thereby producing hydrogen peroxide, wherein the sensitizer is obtained by reacting the specific binding material with a porphyrin that has the formula:

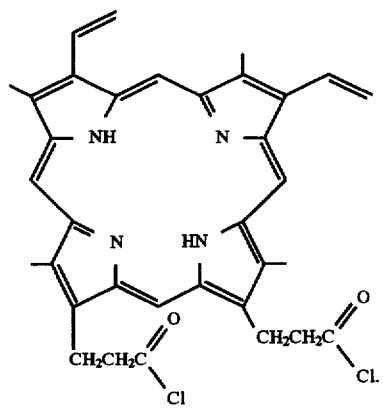

3. A sensitizer conjugate comprising a sensitizer label attached to a specific binding material, that functions as a donor of energy, and an acceptor which uses that energy to evoke a detectable signal, in which the sensitizer label is a moiety that is induced to an excited state by radiation or by chemical or physical stimulus such that it is reactable with, and donates its energy to, (a) molecular oxygen to produce singlet molecular oxygen or (b) a leucodye to form a reduced form that is oxidizable to its original state by reaction with singlet oxygen thereby producing hydrogen peroxide, wherein the sensitizer is obtained by reacting the specific binding material with a porphyrin that has the formula:

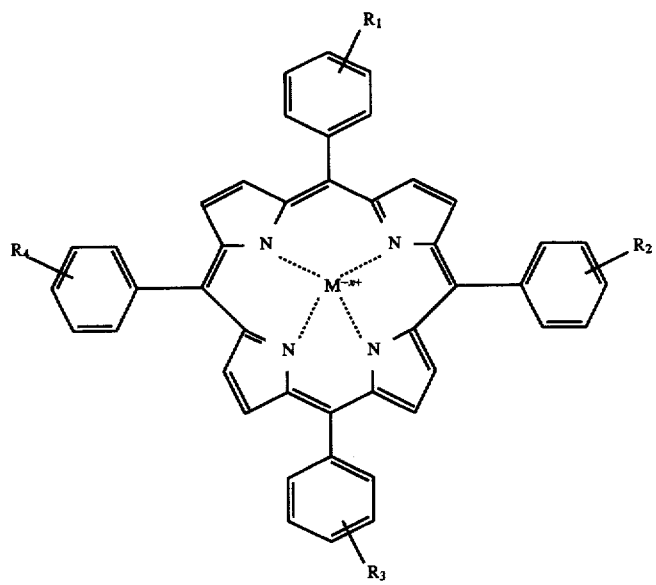

in which M is a polyvalent metal with a valence of x, one or more of the R's are functional groups from the groups from the group consisting of

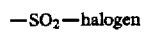 

 

where $R^7$ is the residue of an alcohol

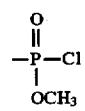 

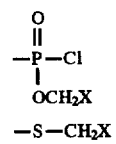 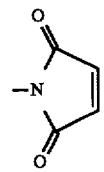

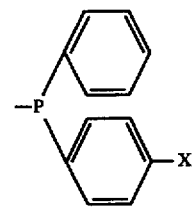 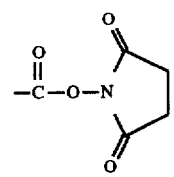

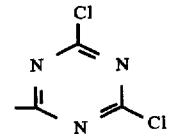

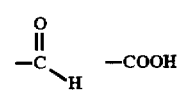

N₃ and other photolabile functionalities

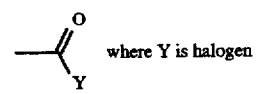

where Y is halogen

4. A sensitizer conjugate comprising a sensitizer label attached to a specific binding material, that functions as a donor of energy, and an acceptor which uses that energy to evoke a detectable signal, in which the sensitizer label is a moiety that is induced to an excited state by radiation or by chemical or physical stimulus such that it is reactable with, and donates its energy to, (a) molecular oxygen to produce singlet molecular oxygen or (b) a leucodye to form a reduced form that is oxidizable to its original state by reaction with singlet oxygen thereby producing hydrogen peroxide, wherein the sensitizer is obtained by reacting the specific binding material with a porphyrin that has the formula:

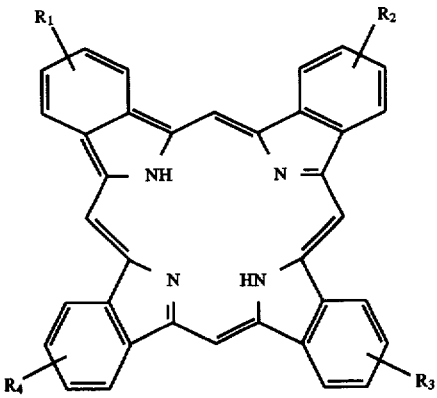

in which one or more of the R's are functional groups from the group consisting of

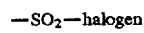 

 

where $R^7$ is the residue of an alcohol

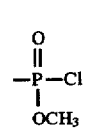 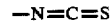

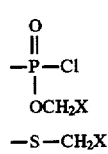
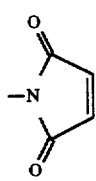
—S—CH₂X
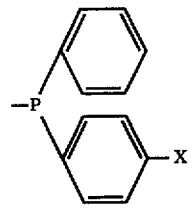
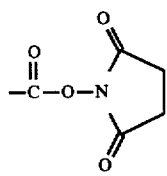
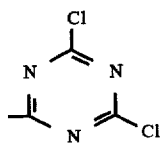
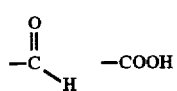
N₃ and other photolabile functionalities
where Y is halogen
* * * * *